US005692501A

United States Patent [19]
Minturn

[11] Patent Number: 5,692,501
[45] Date of Patent: Dec. 2, 1997

[54] SCIENTIFIC WELLNESS PERSONAL/ CLINICAL/LABORATORY ASSESSMENTS, PROFILE AND HEALTH RISK MANAGMENT SYSTEM WITH INSURABILITY RANKINGS ON CROSS-CORRELATED 10-POINT OPTICAL HEALTH/FITNESS/WELLNESS SCALES

[76] Inventor: Paul Minturn, P.O. Box 3287, La Jolla, Calif. 92038

[21] Appl. No.: 473,568

[22] Filed: Jun. 6, 1995

Related U.S. Application Data

[63] Continuation-in-part of Ser. No. 123,872, Sep. 20, 1993, abandoned.

[51] Int. Cl.⁶ .................................................. A61B 5/00
[52] U.S. Cl. .................................................. 128/630
[58] Field of Search .............................. 128/630, 670, 128/700; 364/413.01–413.11

[56] References Cited

U.S. PATENT DOCUMENTS

| | | | |
|---|---|---|---|
| 4,803,625 | 2/1989 | Fu et al. | 364/413.02 |
| 5,396,886 | 3/1995 | Cuypers | 128/630 |
| 5,473,537 | 12/1995 | Glazer et al. | 128/630 |
| 5,492,117 | 2/1996 | Eisenberg et al. | 128/630 |

*Primary Examiner*—Jennifer Bahr
*Assistant Examiner*—Samuel Gilbert
*Attorney, Agent, or Firm*—Lee, Mann, Smith, McWilliams, Sweeney & Ohlson

[57] ABSTRACT

A scientific wellness, optimal health, fitness, and risks quantification, interpretation, correlation and tracking method and system with output reports and summary, and with graduated ranking numerical scales based on the 10-Point Scientific Wellness Scaling and Factoring Formuli. Data gathering forms, devices, documents, sources and questionnaires are divided into different categories of wellness, optimal health, fitness and risks which affect participants arranged so that the data gathered are in the form of graduated numerical scores against a specified and/or ranking scale. The analysis quantification, interpretation, correlation, ranking, tracking and appropriate suggestions are presented in computer printed form for the respective categories in a manner comparing ideal wellness and ultra low-risk conditions against actual conditions of the individual and measurements taken by certified technicians and evaluations and suggestions are graduated and correlated to the scores on the 10-Point Scientific Wellness Scales selected from a data bank according to score. The output report is a computer printed, color-accented, numerically comparative graphic showing how the wellness, optimal health, fitness and risk rating of the participant in the respective categories compares with optimal wellness rating and ranking levels portrayed respectively at levels identified as excellent, good, average, poor, or dangerous, and accompanied by a financial (insurance) incentive feature wherein premiums and deductibles can be adjusted by factoring based upon the unique Insurability Ranking Factors which are cross-correlated to the actual and weighted scores on each of the 10-Point Scientific Wellness Scales and Categories.

20 Claims, 39 Drawing Sheets

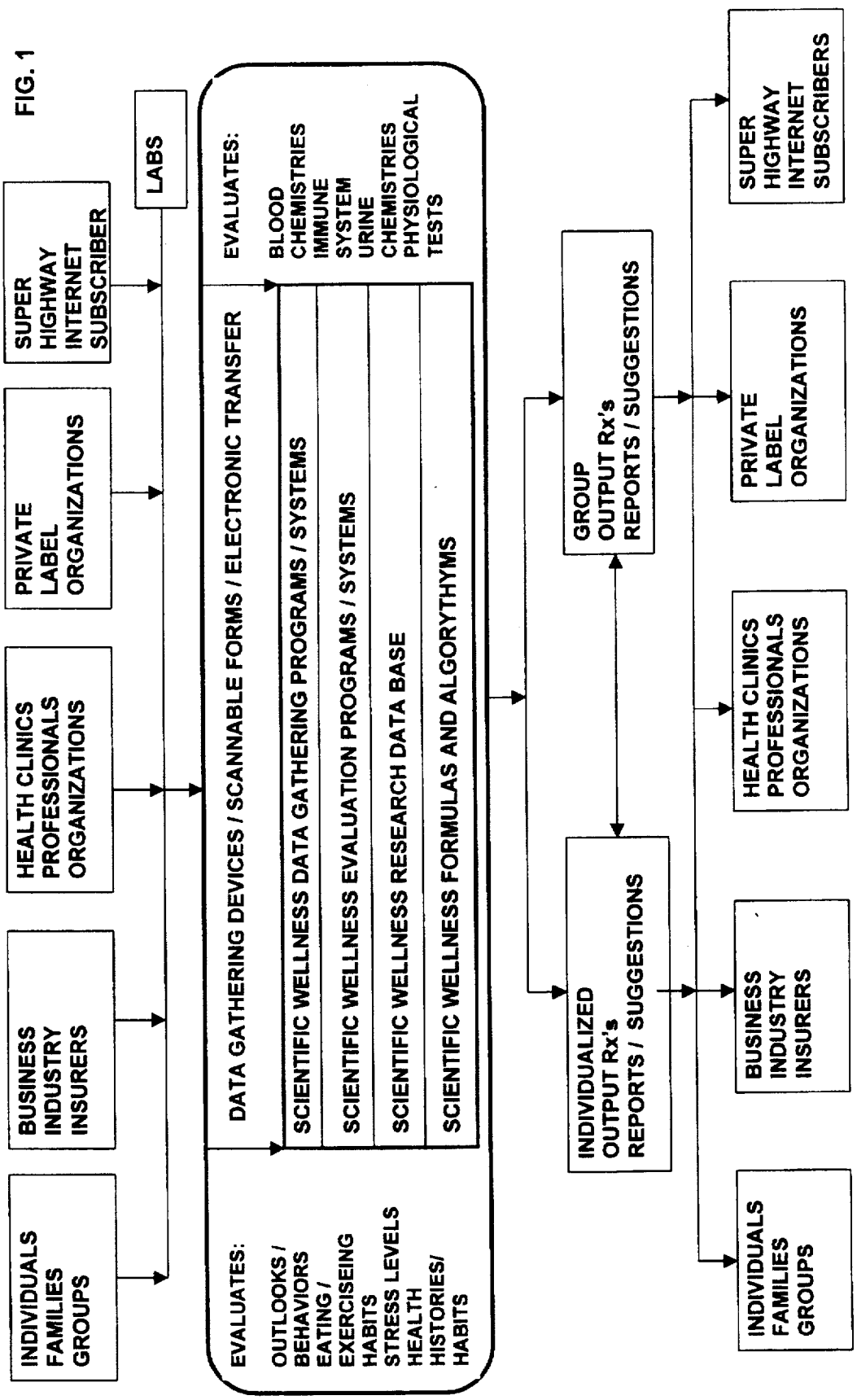

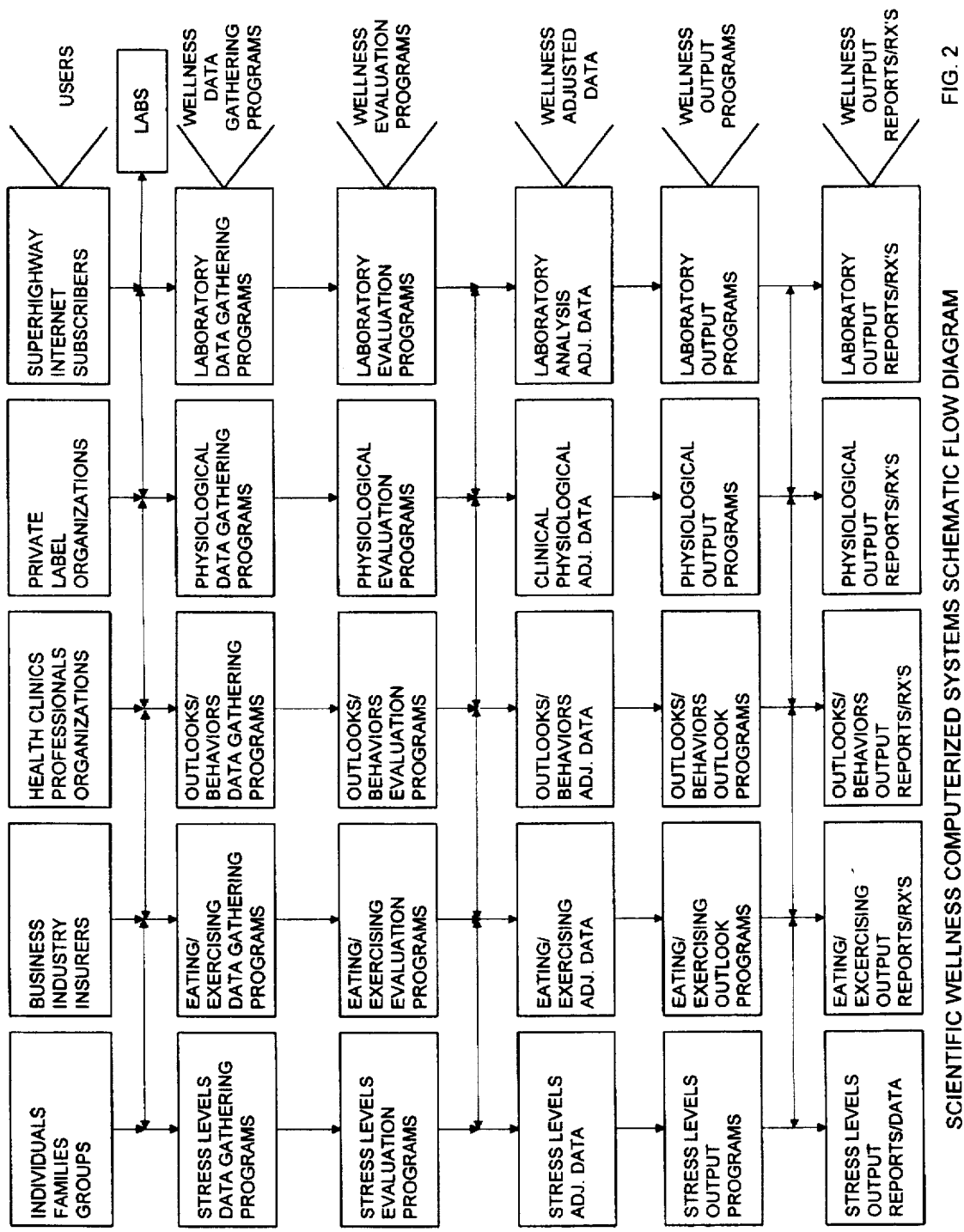
FIG. 2 SCIENTIFIC WELLNESS COMPUTERIZED SYSTEMS SCHEMATIC FLOW DIAGRAM NON-PHYSICAL LIFESTYLE HABITS          "OUTLOOKS / ATTITUDES AND BEHAVIORS"          FIG. 3A

| | DANGER | POOR | FAIR | GOOD | EXCELLENT |
|---|---|---|---|---|---|
| OUTLOOKS / ATTITUDES AND BEHAVIORS | | | | | |
| RATING | 1    2 | 3    4 | 5    6 | 7    8 | 9    10 |

Evaluation and personal recommendations.

Your "OUTLOOKS/ATTITUDES AND BEHAVIORS" rating is 7 - "GOOD". This means you have generally made healthy choices in your basic attitudes/outlooks and behavior patterns. Continue to keep your above average healthy outlooks/attitudes and resultant behaviors on the job so they can reduce your health risks and unnecessary stress. Regular gentle aerobic exercising will also help you maintain your healthy attitudes/outlooks and behaviors and give you increased levels of energy and vitality.

FIG. 3B

NON-PHYSICAL LIFESTYLE HABITS          "COMMITMENT TO WELLNESS"

|  | DANGER | POOR | FAIR | GOOD | EXCELLENT |
|---|---|---|---|---|---|
| COMMITMENT TO WELLNESS | | | | | |
| RATING | 1    2 | 3    4 | 5    6 | 7    8 | 9    10 |

Evaluation and personal recommendations.

Your "COMMITMENT TO WELLNESS" rating is 7 - "GOOD". This means you have a strong commitment to your personal health and fitness. Keep this commitment on the job in order to reduce your health risks and unnecessary stress. Regular gentle aerobic exercising will give you increased levels of energy and vitality.

FIG. 3C

NON-PHYSICAL LIFESTYLE HABITS          "EATING / DRINKING HABITS"

| | DANGER | POOR | FAIR | GOOD | EXCELLENT |
|---|---|---|---|---|---|
| EATING / DRINKING HABITS | | | | | |
| RATING | 1   2 | 3   4 | 5   6 | 7   8 | 9   10 |

Evaluation and personal recommendations.

Your "EATING/DRINKING HABITS" rating is 7 - "GOOD". This means you have made generally healthy choices in the nutritional foods and beverages you consume. It is wise to continue following your good nutritional habits both on and off the job, giving you lots of energy as well as reducing your health risks and unnecessary stress. Regular gentle aerobic exercise will give you increased levels of energy and vitality.

NON-PHYSICAL LIFESTYLE HABITS    "ACTIVITY / EXERCISE HABITS"    FIG. 3D

| ACTIVITY / EXERCISE HABITS | DANGER | POOR | FAIR | GOOD | EXCELLENT |
|---|---|---|---|---|---|
| RATING | 1    2 | 3    4 | 5    6 | 7    8 | 9    10 |

Evaluation and personal recommendations.

Your "ACTIVITY/EXERCISE HABITS" rating is 7 - "GOOD". This means you have made above average healthy choices in the frequency and intensity of the activities and exercises you choose to do. Continue these habits of healthy aerobic activities and exercise off the job to reduce your health risks and unnecessary stress and to increase your levels of energy and vitality.

FIG. 3E

NON-PHYSICAL LIFESTYLE HABITS — "ENVIRONMENTAL HABITS"

| | DANGER | POOR | FAIR | GOOD | EXCELLENT |
|---|---|---|---|---|---|
| ENVIRONMENTAL HABITS | | | | | |
| RATING | 1   2 | 3   4 | 5   6 | 7   8 | 9   10 |

Evaluation and personal recommendations.

Your "ENVIRONMENTAL HABITS" rating is 7 - "GOOD". This means you have made generally healthy choices in the locations where you live and/or work. When you can, get outside in the fresh air of the countryside. Continue to choose clean air and healthy environments on the job to further reduce your health risks and unnecessary stress. Regular gentle aerobic exercising in areas with plenty of fresh air will also give you increased levels of energy and vitality.

FIG. 3F

NON-PHYSICAL LIFESTYLE HABITS          "HEALTH AND SAFETY HABITS"

|  | DANGER | POOR | FAIR | GOOD | EXCELLENT |
|---|---|---|---|---|---|
| HEALTH AND SAFETY HABITS | | | | | |
| RATING | 1    2 | 3    4 | 5    6 | 7    8 | 9    10 |

Evaluation and personal recommendations.

Your "HEALTH AND SAFETY HABITS" rating is 7 - "GOOD". This means you have better than average safety and health habits. Stay committed to these good habits both on and off the job to further reduce your health risks and unnecessary stress. Regular gentle aerobic exercising will give you increased levels of energy and vitality.

NON-PHYSICAL LIFESTYLE HABITS   "NUTRITIONAL SUPPLEMENTAL HABITS"   FIG. 3G

| | DANGER | POOR | | FAIR | | GOOD | | EXCELLENT | |
|---|---|---|---|---|---|---|---|---|---|
| NUTRITIONAL SUPPLEMENTAL HABITS | | | | | | | | | |
| RATING | 1 | 2 | 3 | 4 | 5 | 6 | 7 | 8 | 9 | 10 |

Evaluation and personal recommendations.

Your "NUTRITIONAL SUPPLEMENTAL HABITS" rating is 7 - "GOOD". This means you have made generally healthy choices in the nutritional supplements you consume, such as: vitamins, herbs, minerals and other foods. It is wise to continue following your good nutritional habits both on and off the job. These will give you lots of energy and reduce your health risks and unnecessary stress. Regular gentle aerobic exercising will give you increased levels of energy and vitality.

FIG. 3H

NON-PHYSICAL LIFESTYLE HABITS    "MEDICATIONAL HABITS"

| | DANGER | POOR | FAIR | GOOD | EXCELLENT |
|---|---|---|---|---|---|
| MEDICATIONAL HABITS | | | | | |
| RATING | 1  2 | 3  4 | 5  6 | 7  8 | 9  10 |

Evaluation and personal recommendations.

Your "MEDICATIONAL HABITS" rating is 7 - "GOOD". This means you have made generally healthy choices in the frequency and quantities of over-the-counter or prescription medications you choose to take. Continue these good habits both on and off the job to reduce your health risks and unnecessary stress. Regular gentle aerobic exercise will increase your levels of energy and vitality.

FIG. 31

NON-PHYSICAL LIFESTYLE HABITS

"PERSONAL MEDICAL, HEALTH AND FITNESS HISTORIES"

|  | DANGER | POOR | FAIR | GOOD | EXCELLENT |
|---|---|---|---|---|---|
| PERSONAL MEDICAL / HEALTH HISTORIES |  |  |  |  |  |
| RATING | 1  2 | 3  4 | 5  6 | 7  8 | 9  10 |

Evaluation and personal recommendations.

Your "PERSONAL MEDICAL, HEALTH AND FITNESS HISTORIES" rating is 7 - "GOOD". This means you are fortunate and have had less than the average personal medical conditions in your past. Continuing your good healthy habits on and off the job will further reduce your health risks and unnecessary stress. Regular gentle aerobic exercising will give you increased levels of energy and vitality.

NON-PHYSICAL LIFESTYLE HABITS    "FAMILY MEDICAL / IMMUNE HISTORIES"    FIG. 3J

| | DANGER | POOR | FAIR | GOOD | EXCELLENT |
|---|---|---|---|---|---|
| FAMILY MEDICAL / IMMUNE HISTORIES | | | | | |
| RATING | 1   2 | 3   4 | 5   6 | 7   8 | 9   10 |

Evaluation and personal recommendations.

Your "FAMILY MEDICAL/IMMUNE HISTORIES" rating is 7 - "GOOD". This means you have inherited better than average genetics that can help you maintain your generally healthy habits and choices. Be grateful, you are fortunate. Maintain your healthy habits on the job to minimize your health risks and unnecessary stress. Regular gentle aerobic exercising will give you increased levels of energy and vitality.

FIG. 3K

NON-PHYSICAL LIFESTYLE HABITS          "IMMUNE SYSTEM HISTORY"

| | DANGER | POOR | | FAIR | | GOOD | | EXCELLENT | |
|---|---|---|---|---|---|---|---|---|---|
| IMMUNE SYSTEM HISTORY | | | | | | | | | |
| RATING | 1 | 2 | 3 | 4 | 5 | 6 | 7 | 8 | 9 | 10 |

Evaluation and personal recommendations.

Your "IMMUNE SYSTEM HISTORY" rating is 7 - "GOOD". Until now, your immune system has been better than average because of your generally healthy choices and habits. You can maintain and improve your immune system by consistently taking good care of yourself with eating nutritional foods, taking nutritional supplements that build your immune system, staying away from toxic substances and polluted environments, getting the regular amounts of rest your body needs to rejuvenate itself and by maintaining your healthy outlooks and habits on and off the job thus reducing your health risks and unnecessary stress. Getting regular gentle aerobic exercise will help maintain a healthy immune system and give you increased levels of energy/vitality.

OBJECTIVE PHYSIOLOGICAL TESTS/MEASUREMENTS  "SYSTOLIC BLOOD PRESSURE"  FIG. 4A

Evaluation and personal recommendations.

Your "SYSTOLIC BLOOD PRESSURE" rating is 7 - "GOOD". This means you have managed to maintain healthy outlooks and behaviors that keep the stressors in your life to a minimum. You have also generally made healthy choices in your eating/drinking and exercise habits. Continue following these healthy habits both on and off the job to further reduce your health risks and unnecessary stress. Regular gentle aerobic exercising will give you increased levels of energy and vitality.

OBJECTIVE PHYSIOLOGICAL TESTS/MEASUREMENTS    "DIASTOLIC BLOOD PRESSURE"    FIG. 4B

|  | DANGER | POOR | FAIR | GOOD | EXCELLENT |
|---|---|---|---|---|---|
| DIASTOLIC BLOOD PRESSURE | | | | | |
| RATING | 1    2 | 3    4 | 5    6 | 7    8 | 9    10 |

Evaluation and personal recommendations.

Your "DIASTOLIC BLOOD PRESSURE" rating is 7 - "GOOD". This means you have a cardiovascular system that is above average and have managed to maintain healthy outlooks and behaviors and keep the stressors in your life to a minimum. You have also generally made healthy choices in your eating/drinking and exercise habits. Continue following healthy procedures on the job that will reduce your health risks and unnecessary stress. Regular gentle aerobic exercising will give you increased levels of energy and vitality.

FIG. 4C

OBJECTIVE PHYSIOLOGICAL TESTS/MEASUREMENTS

"RESTING HEART RATE"

| | DANGER | POOR | FAIR | GOOD | EXCELLENT |
|---|---|---|---|---|---|
| RESTING HEART RATE | | | | | |
| RATING | 1  2 | 3  4 | 5  6 | 7  8 | 9  10 |

Evaluation and personal recommendations.

Your "RESTING HEART RATE" rating is 7 - "GOOD". This means you have made generally healthy choices in your lifestyle habits and behaviors resulting in an above average cardiovascular system. The lower you keep your resting heart rate due to wellness and fitness, the longer your heart will last. Keep up the good work and maintain your healthy habits on and off the job. These will reduce your health risks and unnecessary stress. Regular gentle aerobic exercise will give you increased levels of energy and vitality.

OBJECTIVE PHYSIOLOGICAL TESTS/MEASUREMENTS

FIG. 4D

"STRESS MEASUREMENT"

|  | DANGER | POOR | FAIR | GOOD | EXCELLENT |
|---|---|---|---|---|---|
| STRESS MEASURE-MENT | | | | | |
| RATING | 1  2 | 3  4 | 5  6 | 7  8 | 9  10 |

Evaluation and personal recommendations.

Your "STRESS MEASUREMENT" rating is 7 - "GOOD". This means you have made generally healthy choices in your lifestyle outlooks, behaviors and habits resulting in lower than average stress. If you maintain and/or improve your good habits both on and off the job, you will further reduce your health risks and unnecessary stress. Regular gentle aerobic exercising will give you increased levels of energy and vitality.

OBJECTIVE PHYSIOLOGICAL TESTS/MEASUREMENTS    "BODY FAT COMPOSITION"    FIG. 4E

| | DANGER | POOR | FAIR | GOOD | EXCELLENT |
|---|---|---|---|---|---|
| BODY FAT COMPOSITION | | | | | |
| RATING | 1    2 | 3    4 | 5    6 | 7    8 | 9    10 |

Evaluation and personal recommendations.

Your "BODY (FAT) COMPOSITION" rating is 7 - "GOOD". This means you have made generally healthy choices in eating/drinking and exercising habits and in maintaining better than average ratio of fat to muscle mass. The higher you keep your wellness score, the healthier you will be. Keep up the good work and maintain your healthy habits both on and off the job, thus reducing your health risks and unnecessary stress. Regular gentle aerobic exercise will help you maintain a healthy fat to muscle ratio and give you increased levels of energy and vitality.

OBJECTIVE PHYSIOLOGICAL TESTS/MEASUREMENTS

FIG. 4F

"HEIGHT AND WEIGHT RATIO"

| | DANGER | POOR | FAIR | GOOD | EXCELLENT |
|---|---|---|---|---|---|
| HEIGHT WEIGHT RATIO | | | | | |
| RATING | 1  2 | 3  4 | 5  6 | 7  8 | 9  10 |

Evaluation and personal recommendations.

Your "HEIGHT AND WEIGHT RATIO" rating is 7 - "GOOD". This means you have maintained a generally healthy ratio between height and weight because of your above average choices in your lifestyle outlooks, behaviors and eating/exercise habits resulting in lower than average stress. If you maintain and/or improve your good habits both on and off the job, you will further reduce your health risks and unnecessary stress. Regular gentle aerobic exercise will help you keep your good height to weight ratio and give you increased levels of energy and vitality.

FIG. 4G

OBJECTIVE PHYSIOLOGICAL TESTS/MEASUREMENTS

"URINE ANALYSIS"

| | DANGER | POOR | FAIR | GOOD | EXCELLENT |
|---|---|---|---|---|---|
| URINE ANALYSIS | | | | | |
| RATING | 1  2 | 3  4 | 5  6 | 7  8 | 9  10 |

Evaluation and personal recommendations.

Your "URINE ANALYSIS" rating is 7 - "GOOD". This means you have made generally healthy choices in your eating/drinking and exercising habits and in maintaining better than average pH range in your urine. Drink plenty of water and natural juices to help improve your above average score in this vital health factor. The healthier you keep this score due to your wellness and fitness, the healthier you will be. Keep up the good work and maintain your healthy habits on and off the job. These will reduce your health risks and unnecessary stress. Regular gentle aerobic exercise will help you maintain increased levels of energy and vitality.

OBJECTIVE PHYSIOLOGICAL TESTS/MEASUREMENTS

FIG. 4H

"SPUTUM (SALIVA) ANALYSIS"

| | DANGER | POOR | FAIR | GOOD | EXCELLENT |
|---|---|---|---|---|---|
| SPUTUM (SALIVA) ANALYSIS | | | | | |
| RATING | 1    2 | 3    4 | 5    6 | 7    8 | 9    10 |

Evaluation and personal recommendations.

Your "SPUTUM (SALIVA) ANALYSIS" rating is 7 - "GOOD". This means you have maintained a generally healthy lifestyle, outlooks, behaviors, eating/exercise habits and immune system resulting in lower than average risks and stress. If you maintain and/or improve your good habits both on and off the job, you will further reduce your health risks and unnecessary stress. Regular gentle aerobic exercise will help you keep your good health and give you increased levels of energy and vitality.

FIG. 4I

OBJECTIVE PHYSIOLOGICAL TESTS/MEASUREMENTS

"BLOOD CELL ANALYSES"

|  | DANGER | POOR | FAIR | GOOD | EXCELLENT |
|---|---|---|---|---|---|
| BLOOD CELL ANALYSES | | ███████████████████ | | | |
| RATING | 1  2 | 3  4 | 5  6 | 7  8 | 9  10 |

Evaluation and personal recommendations.

Your "BLOOD CELLS ANALYSIS" rating is 7 - "GOOD". This means you have made generally healthy choices in eating/drinking and exercising habits and in maintaining better than average health and immune system. The healthier you keep this score due to your wellness and fitness, the healthier you will be and the longer you will live. Keep up the good work and maintain your healthy habits on and off the job. These will reduce your health risks and unnecessary stress. Regular gentle aerobic exercise will help you maintain your above average health and give you increased levels of energy and vitality.

OBJECTIVE PHYSIOLOGICAL TESTS/MEASUREMENTS

"LUNG VITAL CAPACITY/FORCED VOLUME"

| | DANGER | POOR | FAIR | GOOD | EXCELLENT |
|---|---|---|---|---|---|
| LUNG VITAL CAPACITY/ VOLUME | | | | | |
| RATING | 1  2 | 3  4 | 5  6 | 7  8 | 9  10 |

FIG. 4J

Evaluation and personal recommendations.

Your "LUNG VITAL CAPACITY/FORCED VOLUME" rating is 7 - "GOOD". This means you have made maintained generally healthy lungs because of your above average choices in environmental wellness, lifestyle outlooks, eating/drinking and exercising habits and in maintaining better than average health and your cardiopulmonary system. The healthier you keep this score due to your wellness and fitness, the healthier you will be and the longer you will live. Keep up the good work and maintain your healthy habits on and off the job. These will reduce your health risks and unnecessary stress. Regular gentle aerobic exercise will help you keep your good pulmonary health and give you increased levels of energy and vitality.

LABORATORY ANALYSES    "BLOOD GLUCOSE ANALYSIS"    FIG. 5A

| | DANGER | POOR | FAIR | GOOD | EXCELLENT |
|---|---|---|---|---|---|
| BLOOD GLUCOSE LEVEL | | | | | |
| RATING | 1    2 | 3    4 | 5    6 | 7    8 | 9    10 |

Evaluation and personal recommendations.

Your "BLOOD GLUCOSE ANALYSIS" rating is 7 - "GOOD". This means you have made generally healthy choices in sweets, sugars and regular eating/drinking and exercising habits and in maintaining better than average health. The healthier you keep this score due to your wellness and fitness, the healthier you will be and the longer you will live. Keep up the good work and maintain your healthy habits both on and off the job. These will reduce your health risks and unnecessary stress. Regular gentle aerobic exercise will help you maintain your above average health and give you increased levels of energy and vitality.

LABORATORY ANALYSES  "BLOOD LIVER ANALYSIS"  FIG. 5B

| | DANGER | POOR | FAIR | GOOD | EXCELLENT |
|---|---|---|---|---|---|
| BLOOD LIVER ANALYSIS | | | | | |
| RATING | 1   2 | 3   4 | 5   6 | 7   8 | 9   10 |

Evaluation and personal recommendations.

Your "BLOOD LIVER ANALYSIS" rating is 7 - "GOOD". This means you have maintained generally healthy lifestyle outlooks, behaviors and eating/drinking and exercise habits resulting in above average health and lower than average stress. If you maintain and/or improve your good health habits both on and off the job, you will further reduce your health risks and unnecessary stress. Regular gentle aerobic exercise will help you keep your good health and give you increased levels of energy and vitality.

LABORATORY ANALYSES          "TOTAL BLOOD TRIGLYCERIDES"          FIG. 5C

| | DANGER | POOR | FAIR | GOOD | EXCELLENT |
|---|---|---|---|---|---|
| TOTAL BLOOD TRIGLYCERIDES | | | | | |
| RATING | 1   2 | 3   4 | 5   6 | 7   8 | 9   10 |

Evaluation and personal recommendations.

Your "TOTAL BLOOD TRIGLYCERIDES" rating is 7 - "GOOD". This means you have made generally healthy choices in limited amounts of alcohols, sweets, sugars and regular eating/drinking and exercising habits and in maintaining better than average health. The healthier you keep this score due to your wellness and fitness, the healthier you will be and the longer you will live. Keep up the good work and maintain your healthy habits both on and off the job. These will reduce your health risks of dangerous blood lipids (LDLs) and unnecessary stress. Regular gentle aerobic exercise will help you maintain your above average health and give you increased levels of energy and vitality.

LABORATORY ANALYSES  "TOTAL BLOOD CHOLESTEROL"  FIG. 5D

| | DANGER | POOR | FAIR | GOOD | EXCELLENT |
|---|---|---|---|---|---|
| TOTAL BLOOD CHOLESTEROL | | | | | |
| RATING | 1  2 | 3  4 | 5  6 | 7  8 | 9  10 |

Evaluation and personal recommendations.

Your "TOTAL BLOOD CHOLESTEROL" rating is 7 - "GOOD". This means you have maintained a low-fat diet, above average stress management skills along with generally healthy lifestyle outlooks, behaviors and eating/drinking and exercising habits resulting in above average health and lower than average distress. If you maintain and/or improve your good health habits both on and off the job, you will further reduce your health risks and unnecessary stress. Regular gentle aerobic exercise will help you keep your good health and give you increased levels of energy and vitality.

LABORATORY ANALYSES  "TOTAL BLOOD HDLs"  FIG. 5E

| | DANGER | POOR | FAIR | GOOD | EXCELLENT |
|---|---|---|---|---|---|
| TOTAL BLOOD HDLs | | | | | |
| RATING | 1  2 | 3  4 | 5  6 | 7  8 | 9  10 |

Evaluation and personal recommendations.

Your "TOTAL BLOOD HDLs" rating is 7 - "GOOD". This means you have made generally healthy choices in low-fat foods combined with healthy eating/drinking and above average exercising habits and in maintaining better than average health. The healthier you keep this score due to your wellness and fitness, the healthier your cardiovascular system will be and the longer you will live. Keep up the good work and maintain your healthy habits on and off the job. These will reduce your health risks of dangerous blood lipids (LDLs) and unnecessary stress. Regular gentle aerobic exercise will help you maintain your above average HDLs, your overall health and give you increased levels of energy and vitality.

LABORATORY ANALYSES  "TOTAL CHOLESTEROL TO HDL RATIO"  FIG. 5F

| | DANGER | POOR | FAIR | GOOD | EXCELLENT |
|---|---|---|---|---|---|
| TOTAL CHOLESTEROL TO HDL RATIO | | | | | |
| RATING | 1  2 | 3  4 | 5  6 | 7  8 | 9  10 |

Evaluation and personal recommendations.

Your "TOTAL BLOOD HDLs" rating is 7 - "GOOD". This means you have maintained a generally low-fat diet, above average stress management skills along with natural fiber foods, healthy exercises, lifestyle outlooks, behaviors and eating/drinking habits resulting in above average health and lower than average stress. If you maintain and/or improve your good habits on the job, you will further reduce your health risks and unnecessary stress. Regular gentle aerobic exercise will keep your good health and give you increased levels of energy and vitality.

LABORATORY ANALYSES

"TOTAL BLOOD LDL TO HDL RATIO"

FIG. 5G

| | DANGER | | POOR | | FAIR | | GOOD | | EXCELLENT | |
|---|---|---|---|---|---|---|---|---|---|---|
| TOTAL BLOOD LDL TO HDL RATIO | | | | | | | | | | |
| RATING | 1 | 2 | 3 | 4 | 5 | 6 | 7 | 8 | 9 | 10 |

Evaluation and personal recommendations.

Your "TOTAL BLOOD LDL TO HDL RATIO" rating is 7 - "GOOD". This means you have made generally healthy choices in stress management, alcohols, sweets, sugars and regular eating/drinking and healthy exercising habits and in maintaining a low-fat diet of natural foods combined with natural fiber foods, healthy lifestyle outlooks and behaviors resulting in above average health and lower risks. The healthier you keep this score due to your wellness and fitness, the healthier your cardiovascular system will be and the longer you will live. Maintain your healthy habits on and off the job. These will reduce your health risks of dangerous blood lipids and unnecessary stress. Regular gentle aerobic exercise will help you maintain your above average blood lipid levels and your HDL to LDL Ratio and give you increased levels of energy and vitality.

LABORATORY ANALYSES "IMMUNOCOMPETENCY EVALUATION"

FIG. 5H

| | DANGER | POOR | FAIR | GOOD | EXCELLENT |
|---|---|---|---|---|---|
| IMMUNO-COMPETENCY EVALUATION | | | | ▬▬▬▬ | |
| RATING | 1　2 | 3　4 | 5　6 | 7　8 | 9　10 |

Evaluation and personal recommendations.

Your "IMMUNOCOMPETENCY EVALUATION" rating is 7 - "GOOD". This means you have maintained a generally healthy immune system through a good nutritional diet along with healthy lifestyle, outlooks, behaviors and other eating/exercise habits resulting in above average health and lower than average stress. If you maintain your above average immune system and/or improve your good health habits on and off the job, you will further reduce your health risks and unnecessary stress. Regular gentle aerobic exercise will help you keep your good health and give you increased levels of energy and vitality.

LABORATORY ANALYSES — "IMMUNE SYSTEM (NK) ACTIVITY LEVEL"

FIG. 5I

| | DANGER | POOR | FAIR | GOOD | EXCELLENT |
|---|---|---|---|---|---|
| IMMUNE SYSTEM (NK) ACTIVITY | | | | | |
| RATING | 1    2 | 3    4 | 5    6 | 7    8 | 9    10 |

Evaluation and personal recommendations.

Your "IMMUNE SYSTEM (NK) ACTIVITY LEVEL" rating is 7 - "GOOD". This means you have maintained an above average immune system (NK) activity level with good lifestyle, outlooks, behaviors and healthy eating/drinking habits resulting in above average health and lower than average risks. If you maintain your above average immune system (NK) activity level and/or improve your good health habits both on and off the job, you will further reduce your health risks and unnecessary stress. Regular gentle aerobic exercise will help you keep your good immune system and give you increased levels of energy and vitality.

LABORATORY ANALYSES     "IMMUNE SYSTEM VITALITY AND NKHT3 %"     FIG. 5J

|  | DANGER | POOR | FAIR | GOOD | EXCELLENT |
|---|---|---|---|---|---|
| IMMUNE SYSTEM VITALITY AND NKHT3 % | | | | | |
| RATING | 1   2 | 3   4 | 5   6 | 7   8 | 9   10 |

Evaluation and personal recommendations.

Your "IMMUNE SYSTEM VITALITY AND NKHT3 %" rating is 7 - "GOOD". This means you have made generally healthy choices of lifestyle outlooks and behaviors resulting in above average immune system vitality, NKHT3 %, overall health and lower risks. The healthier you keep this score due to your wellness and fitness, the healthier your immune system will be and the longer you will live. Maintaining your healthy habits both on and off the job will reduce your health risks and unnecessary stress. Regular gentle aerobic exercise will help you maintain your above average immune system vitality and NKHT3 %, and give you increased levels of energy and vitality.

LABORATORY ANALYSES    "AUTOIMMUNOLOGY NK, B, T-CELL COUNTS"

FIG. 5K

| | DANGER | POOR | FAIR | GOOD | EXCELLENT |
|---|---|---|---|---|---|
| AUTOIMMUNO LOGY NK, B, T-CELL COUNTS | | | | | |
| RATING | 1   2 | 3   4 | 5   6 | 7   8 | 9   10 |

Evaluation and personal recommendations.

Your "AUTOIMMUNOLOGY NK, B, T-CELL COUNTS" rating is 7 - "GOOD". This means you have maintained a generally healthy total immune system throughout your body with a healthy nutritional diet along with good lifestyle, outlooks, behaviors, and other eating/drinking habits resulting in above average health levels and lower than average stress. If you maintain your total immune system and/or improve your good health habits on and off the job you will further reduce your health risks and unnecessary stress. Regular gentle aerobic exercise will help you keep your good health and give you increased levels of energy and vitality.

LABORATORY ANALYSES        "IMMUNE T-CELL HELPER/SUPPRESSOR RATIO"        FIG. 5L

| | DANGER | POOR | FAIR | GOOD | EXCELLENT |
|---|---|---|---|---|---|
| IMMUNE T-CELL HELPER / SUPPRESSOR RATIO | ███████████████████████ | | | | |
| RATING | 1    2 | 3    4 | 5    6 | 7    8 | 9    10 |

Evaluation and personal recommendations.

Your "IMMUNE T-CELL HELPER/SUPPRESSOR RATIO" rating is 7 - "GOOD". This means you have made generally healthy choices of lifestyle outlooks and behaviors, and good eating and exercising habits resulting in above average immune T-Cell Helper/Suppressor Ratio, overall health and lower risks. The healthier you keep this score due to your wellness and fitness, the healthier your immune system will be and the longer you will live. Maintaining your healthy habits both on and off the job will reduce your health risks and unnecessary stress. Regular gentle aerobic exercise will help you maintain your above average immune system and give you increased levels of energy and vitality.

PERSONAL HEALTH AND FITNESS PROFILE SUMMARY FIG. 6

| HEALTH AND FITNESS RANKING | DANGER 1-2 | POOR 3-4 | FAIR 5-6 | GOOD 7-8 | EXCEL 9-10 |
|---|---|---|---|---|---|
| SECTION ONE | | | | | |
| PERSONAL LIFESTYLE | | | | | |
| ATTITUDE TOWARD HEALTH AND FITNESS | | | 5 | | |
| BASIC OUTLOOKS AND BEHAVIORS | | | 5 | | |
| ENVIRONMENTAL HABITS | | | | 7 | |
| SMOKING HABITS | | | | | 9 |
| PERSONAL HEALTH AND SAFETY HABITS | | | | 7 | |
| SECTION TWO | | | | | |
| PERSONAL AND FAMILY HEALTH AND FITNESS HISTORY | | | | | |
| PERSONAL HEALTH AND FITNESS HISTORY | | | | | 9 |
| FAMILY HEALTH AND FITNESS HISTORY | | | 5 | | |
| SECTION THREE | | | | | |
| PHYSICAL AND LABORATORY EVALUATIONS | | | | | |
| RESTING HEART RATE | | | 5 | | |
| BODY (FAT) COMPOSITION | | | | 7 | |
| BLOOD PRESSURE – SYSTOLIC | | | 6 | | |
| BLOOD PRESSURE – DIASTOLIC | | | 6 | | |
| STRESS MEASUREMENT | | | | | 9 |
| CHOLESTEROL / HDL RATIO | | | | | 10 |
| SECTION FOUR | | | | | |
| PERSONAL DIET AND NUTRITION | | | | 7 | |
| EATING HABITS | 1 | | | | |
| NUTRITIONAL SUPPLEMENTS | | | | | |
| SECTION FIVE | | | | | |
| PHYSICAL ACTIVITY AND EXERCISE | | | | 7 | |
| HEALTH AND FITNESS RATINGS TOTAL | | | | 7 | |

SCIENTIFIC WELLNESS INSURABILITY FACTORING FOR GRADUATED PREMIUMS/DEDUCTIBLES

FIG. 7

THE MOST OBJECTIVE SCIENTIFIC WELLNESS HEALTH RANKING/TRACKING SCALES/SYSTEM

Scientific Wellness Assessments
Evaluate and Rank the following:

Non-Physical Scales
Scientific Wellness Scores

| Non-Physical Categories | Excelint | Good | Fair | Poor | Dngrous |
|---|---|---|---|---|---|
| Outlooks (Basic Attitudes) and Behaviors | 10 9 | 8 7 | 6 5 | 4 3 | 2 1 |
| * Insurability Ranking Factors | .25 | .50 | 1.0 | 2.0 | 3.0 |
| Commitment to Optimal Health/Wellness | 10 9 | 8 7 | 6 5 | 4 3 | 2 1 |
| * Insurability Ranking Factors | .25 | .50 | 1.0 | 2.0 | 3.0 |
| Eating and Drinking Habits | 10 9 | 8 7 | 6 5 | 4 3 | 2 1 |
| * Insurability Ranking Factors | .25 | .50 | 1.0 | 2.0 | 3.0 |
| Activity and Exercise Levels | 10 9 | 8 7 | 6 5 | 4 3 | 2 1 |
| * Insurability Ranking Factors | .25 | .50 | 1.0 | 2.0 | 3.0 |
| Environmental, Breathing & Smoking Habits | 10 9 | 8 7 | 6 5 | 4 3 | 2 1 |
| * Insurability Ranking Factors | .25 | .50 | 1.0 | 2.0 | 3.0 |
| Health, Safety and Relationship Habits | 10 9 | 8 7 | 6 5 | 4 3 | 2 1 |
| * Insurability Ranking Factors | .25 | .50 | 1.0 | 2.0 | 3.0 |
| Use Food/Vitamn/Mineral/Herbal Supplemnts | 10 9 | 8 7 | 6 5 | 4 3 | 2 1 |
| * Insurability Ranking Factors | .25 | .50 | 1.0 | 2.0 | 3.0 |
| Prescription Medication(s) and Drug Usage | 10 9 | 8 7 | 6 5 | 4 3 | 2 1 |
| * Insurability Ranking Factors | .25 | .50 | 1.0 | 2.0 | 3.0 |
| Personal Medical History | 10 9 | 8 7 | 6 5 | 4 3 | 2 1 |
| * Insurability Ranking Factors | .25 | .50 | 1.0 | 2.0 | 3.0 |
| Family Medical History | 10 9 | 8 7 | 6 5 | 4 3 | 2 1 |
| * Insurability Ranking Factors | .25 | .50 | 1.0 | 2.0 | 3.0 |
| Immune System History | 10 9 | 8 7 | 6 5 | 4 3 | 2 1 |
| * Insurability Ranking Factors | .25 | .50 | 1.0 | 2.0 | 3.0 |

* Multiply Standard Insurance Premium & Deductible Risk Factoring By This Number *

------

| | | | | | |
|---|---|---|---|---|---|
| Total Weighted/Averaged Ranking of Non-Physical Wellness/Risks Levels | 10 9 | 8 7 | 6 5 | 4 3 | 2 1 |
| Total * Insurability Ranking Factors | .25 | .50 | 1.0 | 2.0 | 3.0 |

SCIENTIFIC WELLNESS INSURABILITY FACTORING FOR GRADUATED PREMIUMS/DEDUCTIBLES

FIG. 8

THE MOST OBJECTIVE SCIENTIFIC WELLNESS HEALTH RANKING/TRACKING SCALES/SYSTEM

Scientific Wellness Measurements and Tests Evaluate and Rank the following:

Physiological Scales
Scientific Wellness Scores

| Physiological/Clinical Categories | Excellnt | Good | Fair | Poor | Dngrous |
|---|---|---|---|---|---|
| Blood Pressure(s) | 10  9 | 8  7 | 6  5 | 4  3 | 2  1 |
| * Insurability Ranking Factors | .25 | .50 | 1.0 | 2.0 | 3.0 |
| Resting Heart Rate | 10  9 | 8  7 | 6  5 | 4  3 | 2  1 |
| * Insurability Ranking Factors | .25 | .50 | 1.0 | 2.0 | 3.0 |
| Stress Measurement | 10  9 | 8  7 | 6  5 | 4  3 | 2  1 |
| * Insurability Ranking Factors | .25 | .50 | 1.0 | 2.0 | 3.0 |
| Body (Fat) Composition | 10  9 | 8  7 | 6  5 | 4  3 | 2  1 |
| * Insurability Ranking Factors | .25 | .50 | 1.0 | 2.0 | 3.0 |
| Height and Weight Ratio | 10  9 | 8  7 | 6  5 | 4  3 | 2  1 |
| * Insurability Ranking Factors | .25 | .50 | 1.0 | 2.0 | 3.0 |
| Urine and Sputum Analyses | 10  9 | 8  7 | 6  5 | 4  3 | 2  1 |
| * Insurability Ranking Factors | .25 | .50 | 1.0 | 2.0 | 3.0 |
| Red and White Blood Cell Analyses | 10  9 | 8  7 | 6  5 | 4  3 | 2  1 |
| * Insurability Ranking Factors | .25 | .50 | 1.0 | 2.0 | 3.0 |
| Lung Vital Capacity/Forced Volume | 10  9 | 8  7 | 6  5 | 4  3 | 2  1 |
| * Insurability Ranking Factors | .25 | .50 | 1.0 | 2.0 | 3.0 |

* Multiply Standard Insurance Premium & Deductible Risk Factoring By This Number *

---

| | | | | | |
|---|---|---|---|---|---|
| Total Weighted/Averaged Ranking of Physiological/Clinical Wellness/Risks Levels | 10  9 | 8  7 | 6  5 | 4  3 | 2  1 |
| Total * Insurability Ranking Factors | .25 | .50 | 1.0 | 2.0 | 3.0 |

SCIENTIFIC WELLNESS INSURABILITY FACTORING FOR GRADUATED PREMIUMS/DEDUCTIBLES

FIG. 9

THE MOST OBJECTIVE SCIENTIFIC WELLNESS HEALTH RANKING/TRACKING SCALES/SYSTEM

Laboratory Health/Wellness Analyses
Evaluate and Rank the following:

Laboratory Scales
Scientific Wellness Scores

| Laboratory Categories | Excelnt | Good | Fair | Poor | Dngrous |
|---|---|---|---|---|---|
| Glucose Levels | 10 9 | 8 7 | 6 5 | 4 3 | 2 1 |
| * Insurability Ranking Factors | .25 | .50 | 1.0 | 2.0 | 3.0 |
| Liver Function | 10 9 | 8 7 | 6 5 | 4 3 | 2 1 |
| * Insurability Ranking Factors | .25 | .50 | 1.0 | 2.0 | 3.0 |
| Total Blood Triglycerides | 10 9 | 8 7 | 6 5 | 4 3 | 2 1 |
| * Insurability Ranking Factors | .25 | .50 | 1.0 | 2.0 | 3.0 |
| Total Blood Cholesterol | 10 9 | 8 7 | 6 5 | 4 3 | 2 1 |
| * Insurability Ranking Factors | .25 | .50 | 1.0 | 2.0 | 3.0 |
| Blood HDL Levels | 10 9 | 8 7 | 6 5 | 4 3 | 2 1 |
| * Insurability Ranking Factors | .25 | .50 | 1.0 | 2.0 | 3.0 |
| Ratio of Cholesterol to HDL | 10 9 | 8 7 | 6 5 | 4 3 | 2 1 |
| * Insurability Ranking Factors | .25 | .50 | 1.0 | 2.0 | 3.0 |
| Ratio of LDL to HDL | 10 9 | 8 7 | 6 5 | 4 3 | 2 1 |
| * Insurability Ranking Factors | .25 | .50 | 1.0 | 2.0 | 3.0 |
| Immunocompetency Percentage Test | 10 9 | 8 7 | 6 5 | 4 3 | 2 1 |
| * Insurability Ranking Factors | .25 | .50 | 1.0 | 2.0 | 3.0 |
| Immune System (NK) Activity Test | 10 9 | 8 7 | 6 5 | 4 3 | 2 1 |
| * Insurability Ranking Factors | .25 | .50 | 1.0 | 2.0 | 3.0 |
| Immune System Vitality and NKHT3 % | 10 9 | 8 7 | 6 5 | 4 3 | 2 1 |
| * Insurability Ranking Factors | .25 | .50 | 1.0 | 2.0 | 3.0 |
| Autoimunology NK, B, T-Cell Counts | 10 9 | 8 7 | 6 5 | 4 3 | 2 1 |
| * Insurability Ranking Factors | .25 | .50 | 1.0 | 2.0 | 3.0 |
| Immune System T-Cell Hlpr/Supprsr Ratio | 10 9 | 8 7 | 6 5 | 4 3 | 2 1 |
| * Insurability Ranking Factors | .25 | .50 | 1.0 | 2.0 | 3.0 |

\* Multiply Standard Insurance Premium & Deductible Risk Factoring By This Number \*
================================================================

| | | | | | |
|---|---|---|---|---|---|
| Total Weighted/Averaged Ranking of Laboratory Wellness/Risks Levels | 10 9 | 8 7 | 6 5 | 4 3 | 2 1 |
| Total * Insurability Ranking Factors | .25 | .50 | 1.0 | 2.0 | 3.0 |

SCIENTIFIC WELLNESS PERSONAL/ CLINICAL/LABORATORY ASSESSMENTS, PROFILE AND HEALTH RISK MANAGMENT SYSTEM WITH INSURABILITY RANKINGS ON CROSS-CORRELATED 10-POINT OPTICAL HEALTH/FITNESS/WELLNESS SCALES

RELATED APPLICATION

This application is a continuation-in-part of my U.S. patent application Ser. No. 08/123,872, filed Sep. 30, 1993 now abandoned.

BACKGROUND OF THE INVENTION

1. Technical Field

It is a well known fact that Western or allopathic medicine is based on a sickness rather than wellness paradigm. Most individuals visit a doctor when they are in desperate need of help. For that reason, health care is generally crisis-oriented. Symptoms of pain or dysfunction are an indication that something is wrong. Thus doctors are trained to prescribe toxic pills, cut rather than heal or "make whole," and fix rather than prevent. Too often, major dysfunctions and diseases leading to catastrophic conditions, early aging, serious illness and even death could have been prevented had they been identified before the appearance of devastating symptoms.

The modern hi-tech lifestyle is riddled by stress, dysfunction, early aging and compromised health. It is time to confront alarming national health statistics by addressing them scientifically. The first question asked by a scientist would be, "What caused this situation?" Translated into terms of wellness, Scientific Wellness professionals ask, "What are the causal factors leading to cardio-vascular disease, arteriosclerosis, eating disorders," etc. It seems logical that problems can be solved by exploring their origins. Then and only then can guidelines be established for possible prevention. Science has demonstrated, for example, a strong correlation between lung cancer and smoking. Scientific Wellness professionals also explore the reasons why, for example, people wish to continue smoking even when fully aware of the risks and hazards of nicotine poisoning. By addressing causal factors on all levels, Scientific Wellness Systems can assist individuals in achieving and maintaining optimal health and thus, potentially provide for themselves a more energetic and productive lifestyle. Prevention as a science combined with much earlier detection of diseases is one of the important objects of this invention.

Today, health care costs are a priority for every business, large or small. It is essential that employers seek a cost effective health care plan. Common tools such as gauges in cars and daily planners are used for managing time, but virtually no tools exist for helping one determine how healthy he or she really is. Many businesses utilize risk management concepts in keeping their businesses financially healthy but often ignore the risk management of their most important asset—the optimal health of their employees.

The current popular Wellness Movement dates back to the early 1960s, when America's charismatic president, the honorable John F. Kennedy, spear-headed nationwide interest and attention on physical and mental fitness. Since then, the focus on wellness and optimal health has steadily increased until a recent Gallup Poll estimated that nearly 78% of Americans are personally concerned about their "optimal health and fitness levels."

As a result of many pioneers contributing to the Wellness Movement, today millions are involved in some type of wellness or health improvement program at work, home, the fitness club or elsewhere in their community. The true founders of the Wellness Movement are the numerous health scientists and medical researchers of the past who have searched the world for the keys to optimal wellness and quality longevity. Many of these pioneers spent their lives in search of information and data that would unlock the secrets of achieving and maintaining individual wellness, longevity and a quality life.

Some traveled to distant lands to research and experience first hand the eating and lifestyle habits of native peoples whose average life expectancy was at least 50% longer (with longevity 120 years or more) than the average urban citizen of industrialized communities. In their quest for the modern Fountain of Youth, these pioneers have left a legacy of data and information. The advent of the compact personal computer has made it possible to use this data to address many of the questions concerning optimal health and longevity at a much more sophisticated level. Careful examination of this scientifically processed data has created the potential for establishing personal health and fitness guidelines. Thus, for the first time in history, we have a scientific method for seeking the Fountain of Youth.

One noteworthy group of optimal health scientists and wellness researchers managed to collectively gather a sizable body of scientifically objective data on the general population beginning in the mid-1970s and continuing into the early 1980s. This group of wellness scientists/ researchers consisted of more than 1,000 health care professionals and research scientists (mostly dentists, doctors and university professors) throughout the United States. This research study's first goal was to collectively gather a sizable body of objective physical chemistry data (over 10,000 participants) on perceived optimally healthy people of all ages who had at least a minimum often years or more "completely free" from any form of disease or sickness, including severe headaches, the "Flu" and/or the "Common Cold".

When an individual was found by any one of the 1,000+ researching team of professionals who met the study's "stringent criteria" for the initial sampling of super-healthy individuals, that person was invited to participate in a series of physiological and laboratory tests and measurements that were carefully designed to measure the physical and internal parameters of optimal health and body chemistry. This series included a battery of laboratory tests, including: comprehensive blood, sputum (saliva) and urine chemistries, hair analyses, plus a basic set of physiological measurements, viz., blood pressure, height, weight and posture. The raw data from this initial group of optimally healthy and well people was collected, collated and entered into the "Scientific Wellness and Optimal Body Chemistry Data Base" on a large computer by a dedicated team of health professionals, computer scientists and electronic engineers. This monumental wellness study contributed to the first known attempt at the scientific measurement or quantification of "Scientific Wellness and Optimal Health and Body Chemistries."

Because of the almost impossible base line criteria for this initial "Optimal Health and Body Chemistry" study, it took several years before the first population sampling added up to the target goal of 10,000+ individuals who met the research criteria. Once the initial group of subjects were tested, a carefully selected team of wellness scientists and computer professionals analyzed the raw data and created numerous charts and graphs that established the first hypothetical ranges for optimal body chemistry measurements. The initial set of optimal body chemistry ranges were determined by the statistical means and average deviations from such means of the entire study group of over 10,000 participants.

This team of wellness researchers, health care professionals, computer scientists and electronic engineers next used this set of the optimal body chemistry ranges as the basis of a widespread research project that continued for almost a decade. Over the years, data was collected on body chemistry measurements of millions of Americans (over 3,115,700). This body of computerized data became known as the "Scientific Wellness and Optimal Body Chemistry Data Base." Because of the size of the computers needed to study this data and the number of pieces of data collected, only a few professional researchers ever had access to this large data for any type of wellness research studies.

Throughout the 1970s and early 1980s, these wellness researchers, health care professionals, computer scientists and electronic engineers added others to their team with expertise in such fields as: medical research, fitness, biochemists, nutritionists, exercise physiologists, psychologists, sports physicians and educators. By the early 1980s, this expanded team searched the world for other studies in optimal body chemistry or wellness and was surprised to discover that as yet no one had designed a scientific measuring or quantifying system that could evaluate wellness, optimal health and body chemistry or fitness against any type of optimal ranking set of scales.

The first known "Measurements of Fitness" had its beginnings in the early 1970's at the University of California, San Diego (UCSD). At first, a small research team of fitness professionals and exercise physiologists started collecting data on students, faculty, staff and other community sources of adults in order to determine the key physiological parameters and dimensions of fitness. The people in this research study included athletes, sports minded people, fitness fans and individuals seeking a healthier way of life. During the last ten years or so of the study, the physiological and laboratory data collected included such factors as: age, height, weight, smoking, sex, family health history, personal medical history, activity/exercise levels, blood pressures, body (fat) composition, diet, psychological and mental health parameters (MMPI and CPI Categories) factors, other lifestyle habits, exercise (aerobic) heart rates, oxygen utilization, recovery heart rates, pulmonary vital capacity and forced volume, resting and stress (exercise tolerance) ECGs. In addition, a high percentage (over 59% of the participants) had their blood sugars and toxins, blood cholesterol and triglycerides and other lipid chemistries, proteins and liver function measured.

Ultimately, these Scientific Wellness tests were designed to measure: (1) achievable wellness, (2) present optimal health and fitness levels, (3) presenting major risk factors, and (4) certain medical precursors to catastrophic types of sickness and/or disease. The original instruments were designed and developed from extensive scientific research coupled with extensive field tests. The scores from the entire battery of Scientific Wellness tests and measurements were also compared with existing health and medical norms, peak performance, optimal levels of total health and fitness, precursors of illness or disease and known risk factors. At first, the battery of tests and measurements were extremely comprehensive, complex (over 68 different types of testing procedures) and expensive to administer. The original purpose behind these tests was to monitor all known factors believed to indicate a high level of health and fitness and peak performance. The tests were first aimed at determining prime cardiovascular fitness and/or potential diseases, thereby predicting one's statistical chances of future heart attacks and/or strokes. Scientific information from state-of-the-art exercise and fitness physiology and cardiac rehabilitation technologies was combined with considerable research in conjunction with these wellness testing systems in order to determine the specific factors that objectively indicate levels of "optimal health and fitness." Over the years, thousands were tested for their levels of fitness and cardiac risk with these measurements. Other population groups were measured for their physiological and psychological health and were added to this early collection of dam. The size of the raw data collected at UCSD and elsewhere for more than a decade had grown into the tens of thousands, but it was never evaluated or analyzed for possible correlations of any type until the early 1980s when this data was discovered gathering dust in one of the archival storage lockers on the UCSD campus.

At UCSD alone, more than 12,400 people were given this battery of comprehensive tests and measurements to determine their cardiovascular fitness and wellness levels as well as major risks factors (if any). Surprisingly, most of these individuals tested (over 63%) were later determined to be "above average to excellent" examples of "optimal physiologically determined health and fitness." The gender balance for this group was nearly equal. Their demographic data included a wide range of ages, ethnic origins, socio-economic and educational levels. Many (over 37%) received annual evaluations from four to twelve times during the first decade of this UCSD study so that some comparative trends were possible once the data had been entered into the computer for statistical analyses.

Many of the participants in this UCSD fitness study were from other parts of the world and new to the area, having been attracted to the healthier beach and "fitness" lifestyles available along the coasts of California. These population demographic factors meant that the individuals being sampled for this study generally represented a reasonable cross-section of those Americans who are healthy and fit. This research also included the largest comparative study on body (fat) composition in the U.S. (over 11,000+). Subcontaneous fat tissue was first quantified using the gold standard, viz., the underwater hydrostatic measurements. The same people were then tested by the four-point skinfold caliper measurement system. In both cases, in order to achieve the smallest margins of error, it was important to have all of the tests/measurements taken by well trained exercise physiologists or health technicians.

The results of these two body (fat) composition measuring methods were compared and contrasted for accuracy. In order to establish baseline standards for the comparative study, it was decided that the hydrostatic evaluations would be considered the most accurate of the two measurements, viz., as a base line number for a comparative analysis of the four-point skinfold caliper measurement's relative accuracy to the hydrostatic measurement. When the results of the study were tabulated, the researchers found the four point skin caliper measurements averaged about a 97% accuracy throughout the entire group, but only if these measurements were taken by well trained technicians. This substantially demonstrated that the four fold skin caliper measurement when done by well trained technicians was a reasonably accurate scientific assessment of a person's body (fat) composition. The only exception to this was experienced when measuring the serious obese person who had an excess of 20% over the ideal body fat) composition range. In these cases, the skin fold tests had a slightly higher percent of error.

Another study at UCSD focused on cardiac risk assessment of people who exhibited a wide range of fitness levels. In this study, the following fitness/risk evaluations were included in the original battery of tests and measurements that were administered by the UCSD cardiac researchers. A short cardiac risk questionnaire assessed: (1) both personal and family medical histories, (2) a few personality and psychological factors, (3) dietary habits, (4) exercise levels, (5) smoking, and (6) working and living environment. Technicians took specific physical tests and measurements which included: blood pressures (systolic/diastolic), body (fat) composition, pulmonary forced volume and forced vital capacity, resting heart rate, exercise heart rate, recovery heart rate, oxygen utilization, flexibility and strength, resting ECG, stress ECG (exercise tolerance type), strength test (eliminated after 5 years), in addition to important blood chemical laboratory analyses, which included: total blood cholesterol and triglycerides, HDL, LDL, glucose, proteins and liver function.

Also, during the late 1970's and early 1980's, a number of medical research groups composed of primarily medical trained experts began to develop a myriad of Health Potential and Risk Appraisal Instruments, called HPSs or HRAs, i.e., "Health Potential Studies and Summaries" or "Health Risk Appraisals or Assessments", respectively. By 1986 over 250 HPSs and HRAs existed. All of them were attempts to measure risk(s) factors in the general population. Unfortunately these HPSs and HRAs were field tested and found useless in the measurement of Wellness, Optimal Health, Body Chemistry or Fitness, because they had no "optimal health standards" to go by and were solely based on data from the Center for Disease Control Data (CDC) on illnesses or the widely accepted and standardized government and insurance morbidity and mortality tables. In their attempt to discover and reduce major risk factors, all of the HPSs and HRAs have failed to quantify or measure optimal wellness. Many medical, wellness and optimal health researchers are convinced that most if not all of these HPSs and HRAs have also failed to scientifically quantify or predict any of the more serious catastrophic risk(s). Otherwise, they would be more widely utilized by the actuaries of the major insurance companies to manage and reduce their risk(s) of future major large dollar claims.

The Challenge of Measuring "Health Risks" in the 20th Century

Until the advent of the personal computer and data base management systems for "PCs" in the late 1970s and early 1980s, every attempt to discover, field test, evaluate, quantify and/or predict future health risks failed actuarially or mathematically for at least four major reasons.

First. The measurement of such risk factors was extremely limited because they were not measured, correlated, compared or tracked against any optimal health and fitness scales.

Second. These HPSs and HRAs were exclusively based on the generally accepted assumption that the absence of most major risks (or their associated risk factors) meant that an individual could be generally classified as low risk or labeled in "EXCELLENT HEALTH."

This assumption, however, was faulty for two reasons: (a) it was much too simplistic, and, (b) it turned out to be too good to be true. Extensive research has found that many erroneous judgments of being in "EXCELLENT HEALTH" occurred when the tests showed an absence of major risk factors or symptoms at that precise moment, where in fact, that person might be a walking time bomb of poor health, (with no apparent symptoms or active conditions requiting immediate medical attention).

Third. All of the risk and medical diagnosing systems and procedures used as background for these HPSs and HRAs were limited to assessing only major SYMPTOMS or active CONDITIONS, but none were designed to discover root causes associated with serious sickness, disease or death. The medical health care delivery systems attempted (though unsuccessfully) to correlate these major risk factors to the insurance morbidity and mortality tables.

Fourth. In the final analysis, ALL of the HPSs and HRAs (all 300+ at this time) failed to statistically predict even minor future risk(s) factors and/or claims because the HRAs and HPSs had been correlated only to the CDC data and/or to the "morbidity and mortality tables." Throughout these years, medical researchers did not attempt to measure optimal health or fitness, since it was assumed that these were equivalent to the absence of active symptoms or conditions.

HPSs and HRAs Are Still Solely Based on Morbidity/Mortality Tables

More than 300 health potential and risk appraisal systems currently exist. Most (including Fuller et at, U.S. Pat. No. 4,464,122) are only compared or contrasted to the popular CDC and/or government/insurance risk statistics on death and disease (mortality and morbidity statistics). Because these systems do not compare to any measured, quantified or validated wellness or optimal health and fitness factors or data, but rely solely on limited risk data for their evaluation, ranking and interpretation of ultra low-risks, wellness or optimal health and super-fitness cannot be scientifically measured. Scientific Wellness alone allows individuals to fully explore their achievable wellness and optimal health levels.

All of the popular (over 300+) Health Potential Summaries and Risk Appraisal Systems (HPSs and HRAs) attempting to discover and measure health risk factors which are believed or known to result in morbidity and/or mortality are still correlated only to the CDC data and/or formulations (algorythmns) associated with the standardized government and insurance mortality and morbidity indices. Some of the HPSs and HRAs are aimed at early detection and prevention of the most serious morbidity and mortality factors. Others unsuccessfully attempted to correlate the HPS or HRA questionnaire items to future health potential, and/or to predictable longevity or a few to life extension factors.

HPSs and HRAs Are Unable to Accurately Measure Optimal Wellness or Predict Future Risk (s)

Without exception, all of the myriad of HPSs and HRAs (300+) purporting to measure health risk factors in either individuals or in groups have the same basic weaknesses. The most significant limitation of the HPSs and HRAs is the fact that without exception, they are totally unable to measure, quantify or track gradual or small incremental changes in wellness and/or compare any of the major risk(s) to optimal levels of health or fitness. This is because they have no wellness ranges and are limited to a 2-Point range (not at-risk or at-risk) or a 3-Point range (low-risk, medium/ average-risk, and high-risk). The HPSs and HRAs can generally identify whether a person is "At High-Risk" or "At Average-Risk," but only for this moment (not for later today, or tomorrow, or next month or a year from now, etc.). However, none of the HPSs or HRAs can identify or quantify the person who is "Not At Risk". Because of this serious drawback, the HPSs and HRAs have been of little use to risk managers or insurance actuaries as any type of risk management device and/or predictor of future claims. The reasons for this are simple to understand: (1) HPSs and HRAs are essentially based on a Two-Point or Three-Point Scaling System (even if they use Ten-Point Risk Scales) because each participant is tested and judged to be either "At Risk" or "Average Risk". None of them are able to identify, measure or track gradual changes in persons "Not At Risk". (2) Mathematically, all the HPSs' and HRAs' correlative formulations compare the risks only to the CDC data and/or to morbidity and/or mortality data and associated indices (thus the absence of such risks means that the person must be in "excellent" [?, ?, ? ]health); (3) Compared to the Ten-Point Scientific Wellness Scaling System, the HPSs and HRAs are only able to quantify or distinguish the lower end of the 10-Point Scientific Wellness Scales, viz., between a "1" (very high risk) and a "3" (poor health); (4) None of the HPSs and HRAs (no exceptions) are able to measure, identify or track between the "4s" up to "10s" on the Ten-Point Scientific Wellness Scaling System To These HPSs and HRAs, the "4s" and the "10s" appear the same mathematically; (5) Thus the HPSs and HRAs miserably fail as early detection or prevention devices for most serious morbidity and mortality conditions, because of their inability to quantify or predict either Optimal Wellness or Ultra-Low Risk(s) Levels; and, (6) The HPSs and HRAs will never be able to quantify optimal health/fitness or serve as major risk management devices, because the "Absence of Major Risks" bears no relationship to measurements of "Optimal Wellness."

2. Description of Prior Art

More than 300 health potential studies and summaries (HPSs) and health risk appraisal systems (HRAs) currently exist. Most are compared to only the risk statistics on death and disease (mortality and morbidity). Because these systems do not compare to any quantified or validated Scientific Wellness or Optimal Health and Fitness Data but rely on limited risk only data for their interpretation of risks, the parameters of optimal wellness, health and fitness cannot be measured or small changes tracked by any of them. Scientific Wellness alone allows individuals the ability to fully and objectively explore their achievable levels of wellness and optimal health.

Only one health potential summary and incentive system (HPS) has filed for a patent (invented by Fuller et at., U.S. Pat. No. 4,464,122. However, this invention cannot be compared to the new and improved Scientific Wellness System of the present invention because Fuller assesses only a limited number of subjective life-style health risk factors and no objective physiological or laboratory health risk factor. HPS cannot objectively or scientifically measure, quantify or evaluate the most important of the psychological, physiological or laboratory wellness parameters; and thus has no evaluative ability, or system, or questionnaires, or data gathering forms and devices/ documents, or comparative scientifically validated wellness parameters or data bases; and consequently does not have any capability of measuring or quantifying any of the upper ranges of the approximately 33+ factors of optimal wellness, health or fitness.

Fuller et at., U.S. Pat. No. 4,464,122, is therefore limited to measuring health potential and/or risks solely based on comparisons to the CDC data base of risks and statistics on death and disease (mortality and morbidity). Because this prior invention has no empirical or CDC data of quantified and/or validated optimal wellness, health or fitness data to contrast or compare with, it is limited to the assessment and evaluation of only average to high health risks, or to the interpretation of average to high risks and not to the assessment, evaluation or interpretation of "true" health potential, optimal wellness, ultra-low health risks or fitness. Typical of the approach taken by this prior invention has been to take some personal data on a given individual and compare that data against the CDC data base of risks and statistics on death and disease (mortality and morbidity) and with other people in a normative(but not measured to be optimally healthy) database who have had similar risks. Health expectations from the CDC mortality and morbidity data base and the average health normative risk database profile that most nearly matches the individual's responses to the health potential questionnaire have then been fed back to the user in such forms as achievable health potential and actual age vs. appraisal health age and achievable age, and with such extremely generalized recommendations for behavior changes as reducing the amounts of dietary cholesterol and saturated fats, salt, and calories, etc.; and lowering the use of alcohol, tobacco and drugs; and reducing the effects of stress caused by life events; and increasing low-fat foods, exercise, stretching, vitamin and mineral consumption, presumably resulting in increased odds for a longer and healthier life.

The HPS invention, however, has a fatal flaw in its system, because it cannot quantify health potential above and beyond the generalized average health potential of CDC's morbidity and mortality database and statistics of only average to poor healthy (not super-healthy) persons. Fuller does not have a wellness database of super-healthy people against which to compare or contrast risk levels or quantify future health potential or achievable age. Perhaps this is why this instrument has not been widely used during the last decade in this technical field.

The Scientific Wellness System and Scales used in the study of the present application are not the same as any of the other health potential summaries (HPSs) or health risk appraisals (HRAs) which are solely backed and based on limited average health and/or death and disease data from CDC and/or the morbidity and mortality indices and statistics of the government and/or the insurance tables. The average health and/or death and disease data and/or the CDC data and/or the morbidity and mortality indices and statistics are really "after the fact" of either disease or death. Neither the average health and/or death and disease data and/or the CDC data and/or the morbidity and mortality indices and statistics offer any useful data or information to quantify or track levels of optimal health or fitness, and/or any useful data in the earliest detection of risk trends, and/or any type of comparative data to evaluate or interpret optimal health and wellness levels. Thus, the average health and/or death and disease data and/or the CDC data and/or the morbidity and mortality indices are unable to assist in the quantification of any wellness or optimal health or fitness parameters.

It is very important to understand that the absence of risky behaviors or conditions which could lead to either to morbidity and/or mortality is not equivalent (mathematically and/or practically) to or the same as high level wellness or optimal health and fitness. In sharp contrast to all of the HPSs and HRAs, ALL of the Scientific Wellness Ranking Scales and their Ranges are based both on living, super-healthy human beings that were tested, measured and quantified as being super-healthy, extremely low-risk, capable of peak performance and living lives of optimal health and fitness. Many of these subjects were tested over and over during a 30 year period of time. Now a person can know exactly what is his or her ideal, based on over 30+ years of research, as well as at least 30 or 40 years of archeological research into cultures that enjoyed great longevity in excess of 150+ year life spans.

Today, controlling health care costs are mandatory for every business, large or small. It is urgent that employers seek a cost effective graduated wellness health care plan. Employers can significantly reduce costs related to excess medical utilization by early detection of preventable risks, which are likely to become claims. Results from individuals and group testing will clearly identify the type of program interventions needed. Scientific Wellness offers a starting point and thereafter becomes the yardstick that measures the benefit of any individual or corporate health improvement program.

Generally, more than fifty per cent of health care costs are lifestyle-related and therefore preventable. Individual consumers interested in optimal health and fitness need to identify specific areas for personal improvement. Responsible managers in business need to develop systems to manage the optimal health of their employees, not only to save costs but also to save fives. The Scientific Wellness tracking system provides the guidebook for becoming one's healthy best.

Scientific Wellness offers a proven Advanced Risk Management System (ARMS) which identifies each company's needs. Each ARMS Program is customized with specific educational health care programs and tracking systems, which offer incentives for making healthier outlooks and lifestyle changes. This is the first plan to successfully quantify and separate high risk from medium risk from average-risk from low-risk from ultra low-risk groupings. Scientific Wellness is a state of the art program that offers:
Base Line Measurements to Determine Initial Needs and Risk Levels
Periodic Measurements to Predict Achievable Successes and Savings
A User Friendly Computerized Risk Management Tracking System
Periodic Economically Correlated Reports on Program Successes Employees may choose to participate in the Scientific Wellness Graduated Levels of Health Care Services. Premiums and deductibles for Graduated Levels of Health Care are based on unique Scientific 10-Point Wellness Scales and Insurability Factorings. This scientific monitoring program has a built-in cost effective Win/Win incentive for participants. As health habits improve, benefits increase, and premiums and deductibles may be reduced.

BRIEF SUMMARY OF THE INVENTION

Objects of the Invention

Accordingly, it is an object of the present invention to provide a new, scientifically objective, improved, quantifiably validated and advanced system and method for measuring, evaluating, interpreting, quantifying and tracking small incremental changes in optimal wellness, health and fitness levels.

It is further an object of the present invention to provide a new, scientifically objective, improved, quantifiably validated and advanced system and method for measuring, evaluating, interpreting, quantifying and tracking small incremental changes in both major and minor health risks and deteriorating or debilitating changes in the immune system.

It is also an object of the present invention to encourage and facilitate a maximum number of participants in making quantifiable positive improvements in their measured levels of optimal wellness, health and fitness through changes in outlooks and attitudes, nurturing/healthy relationships, self-love, improved mental/emotional health and balance, better eating/drinking and gentle exercise habits and other important improvements in lifestyle behaviors.

It is an additional object of the present invention is to provide a new, scientifically objective, improved, quantifiable validated and advanced system and method for measuring, evaluating, interpreting, quantifying and tracking small incremental changes wherein the subject matter of the areas of assessment and evaluation are expanded to include measurements and evaluations of the most important psychological, physiological and laboratory wellness parameters utilizing many different data gathering forms, devices, documents and sources of data, physiological measurements taken by American Wellness Association (AWA) certified technicians, laboratory blood and urine analyses, all of which are compared to scientifically quantified and validated wellness parameters and data bases measuring, evaluating, correlating, interpreting, quantifying and tracking up to approximately 33+ factors of optimal wellness, health or fitness in order to provide a more objective and comprehensive variety of information for analysis.

Another object of the present invention is to provide a new, objective, improved, quantifiable, validated and advanced system and method for measuring, evaluating, interpreting, quantifying and tracking small incremental changes in eating and exercise habits cross-correlated to the physiological and laboratory tests and measurements of optimal wellness, health and fitness.

Still another object of the present invention is to provide a new, objective, improved, quantifiable, validated and advanced system and method for measuring, evaluating, interpreting, quantifying and tracking small incremental changes in the psychological, physiological and biochemical effects of life's stressors plus any changes in the sources, intensity levels and coping skills of the participant with regards to stress or distress levels.

It is a further object of the present invention to provide in a new, objective, improved, quantifiable, validated and advanced system and method for measuring, evaluating, interpreting, quantifying and tracking small incremental changes in optimal wellness, health and fitness a means for cross-correlating the different expanded areas of investigative tests and measurements and the resulting information so that the evaluative commentary and suggestions to the participant are directed to specific categories that have been taken into consideration as conditions outside of such categories but which have an actual impact upon the evaluative commentary and suggestions given to the participant.

Further included among the objects of the present invention is to provide a new, objective, improved, quantifiable validated and advanced system and method for measuring, evaluating, interpreting, quantifying and tracking small incremental changes in optimal wellness, health and fitness which includes a well designed graphically pleasing persuasively presented personal report in a manner such that the participant need have no knowledge or appreciation of the sophisticated data gathering forms, devices, questionnaires, documents or sources of information and/or the computerized suggestions but need only be capable of understanding the meaning of the simple 10-Point Scientific Wellness Scales and the reading of simple, laymanlike language and figures, brought to the participant's attention in a graphic fashion which itself is designed and formulated to have a positive and persuasive effect upon the ultimate compliance of the participant.

Still another object of the present invention is aimed at assisting the participant understand the purpose, meaning and importance of the Scientific Wellness battery of tests and measurements of optimal wellness, health and fitness and the reasons for combining attitudinal, psychological, physiological and laboratory assessments for greater accuracy and objectivity in analyses, interpreting and tracking of both positive and negative changes in major health risks and/or levels of optimal wellness, health and fitness.

It is a further object of the present invention to help each participant understand the meaning of serious health risk-taking in relation to personal life-style and health habits and behavior patterns and that how a person lives and believes often determines the diseases experienced and how the person may die; which demonstrates through concepts of risk management the effects of risk-taking, showing that personal unhealthy habits and behavior risks not only add to one's problems but compound one another; which personalizes the health and lifestyle habits and risks to help the participant realize that such risks can apply to the participant, which indicates by the commentary and suggestions the relative importance of health and lifestyle risks, thereby enabling the participant to be able to make wise choices as to which habits, behaviors and risks to eliminate; which by commentary and suggestions conveys a sense of urgency to assist in motivating the individual to make positive and measurable changes, and which provides an on-going incremental measurement of improved wellness and reduced risks if certain poor health attitudes and habits are altered or eliminated.

With these and other objects in view, the present invention consists of the arrangement and combination of the various Scientific Wellness tests and measurements providing raw data which is inputed into the computer, processed, compared and contrasted to the quantified and validated and frequently updated and revised proprietary wellness and optimal health and fitness database, resulting in an individualized output report which graphically indicates each rank and rating of wellness levels on a series of up to 33+ or more 10-Point Wellness Scales with simple, appropriately ranked personalized evaluative comments and suggestions in laymanlike language and figures, brought to the participant's attention in a graphic fashion which itself is designed and formulated to have a positive and persuasive effect upon the ultimate compliance of the participant together with other aspects of the system, serving as an example only of one or more embodiments of the invention, whereby the objects contemplated are attained, as hereinafter disclosed in the specification, and pointed out in the appended claims.

BRIEF DESCRIPTION OF THE DRAWINGS

The invention is described in greater detail in the following description of an example embodying the best mode of the invention, taken in conjunction with the drawing figures, in which:

FIG. 1 is a block diagram illustrating a preferred form of the invention,

FIG. 2 is a comprehensive schematic diagram showing the system according to the invention and interconnections and comparative correlations of the various aspects of the invention, FIGS. 3A through 3K illustrate examples of non-physical parameters of Scientific Wellness, FIGS. 4A through 4J illustrate examples of physiological, clinical measurements of Scientific Wellness, FIGS. 5A through 5L illustrate examples of laboratory biochemical analyses of Scientific Wellness, FIG. 6 is an example of a portion of an individualized Scientific Wellness summary evaluation and ranking chart, FIG. 7 is a reproduction of a portion of the ranking chart setting forth Scientific Wellness insurability ranking factors for non-physical data, FIG. 8 is a portion of the ranking chart setting forth Scientific Wellness insurability ranking factors for physiological data, and FIG. 9 is a portion of the ranking chart with Scientific Wellness insurability ranking factors for laboratory data.

DESCRIPTION OF EXAMPLES EMBODYING THE BEST MODE OF THE INVENTION

The Scientific Wellness System offers the following unique features:

It allows an individual to be compared to optimally healthy groups.

It emphasizes positive mental outlooks as important predictors of risk.

It contains eight global categories of health status, making it among the most comprehensive in use today.

It allows for the measurement of the impact of stress on the physical systems of the body and immune system.

It dramatically improves the ability to predict an individual's future health, medical utilization and resulting benefit from any health improvement program.

GLOBAL CATEGORIES

Healthy Relationships

Mental/Emotional/Psychological Wellness

Physical and Genetic Health

Optimal Health and Fitness Habits/Behaviors

Physical Measurements

Laboratory Blood and Urine Evaluation

Outlooks/Attitudes/Self-Love

Special Immune Defense Evaluation

Results from an individual's or group's assessment are compared to a Scientific Wellness and optimal health/fitness data base. This comparison objectively measures to all significant categories of Scientific Wellness and health risk levels on a series of 10-Point Scales. Only the bottom three points of the Scales are related to illness and the top seven points are related to optimal health and wellness. A report with interpretations and recommendations is generated and then communicated to the individual and/or group highlighting specific areas of wellness and risk and recommending corrective strategies. Tracking wellness improvements and/or changes in levels of health risk at set intervals allows consistent objective measurement of both improvements and risks for many years.

The invention is pointed out with particularity in the appended claims. However, other features of the invention will be best understood by referring to the following detailed description of the preferred embodiments.

FIG. 1 shows a schematic block diagram illustrating a preferred embodiment of a sophisticated data processing software system and programs incorporating many different data gathering forms, devices, questionnaires, documents and sources of both wellness and health risk data. These may include some or all of the following: (1) subjective cross-correlated non-physical evaluations of optimal health and fitness data gathering forms, devices, questionnaires, documents and sources; (2) objective cross-correlated physiological tests and measurements from various data gathering forms, devices, documents and sources, and recorded by trained and certified AWA technicians; and, (3) the most objective cross-correlated laboratory internal wellness data from a variety of data gathering forms, devices, documents and sources entered and/or merged with laboratory electronic data transfer into the Scientific Wellness Database System of the present invention. All of the wellness data is compiled; checked for validity; stored as an inventory of wellness, health, fitness and risk-related knowledge; and, evaluated, analyzed and compared to the wellness database. The software system and programs are capable of rapid wellness and laboratory data entry and processing. The individualized output wellness reports contain a series of visual depictions each having analysis information categorized on 10-Point Scientific Wellness Scales as well as highlighted suggestions and recommendations that are graphically portrayed and can either be printed on compatible laser printers or downloaded for processing by a high-speed computer printing service company. Collecting accurate data has demonstrated to be of surprisingly importance, because it often determines whether the participant will make any positive behavior or habit changes to improve their achievable levels of optimal wellness, health and fitness.

FIG. 2 is a comprehensive schematic diagram of the various computer components, the system and programs showing the interconnections and the comparative correlations of each category required by the wellness measuring and tracking system. In an embodiment of the invention chosen for the purpose of illustration, the methods of preparing scientific wellness assessments involves the employment of many different data gathering forms, devices, questionnaires, documents and sources of wellness and health risk data. These begin with a predetermined battery of non-physical evaluations of lifestyle/outlooks/psychological behaviors and habits. The data from the non-physical parameters can be collected from a series of data gathering forms, devices and documents. The subjective non-physical data is then combined with the more scientific objective measured data collected from a series of data gathering forms, devices, documents and sources including a series of technician taken clinical and physiological tests and measurements, such as: resting/active/recovery heart rates; blood pressures; stress levels; body (fat) composition; height and weight ratio; quick analyses of urine, sputum and the red and white blood cells, etc.; and, the vital capacity/forced volume of the lungs all of which can be measured by qualified and certified wellness technicians. Then, both the subjective wellness data derived from the non-physical data gathering forms, devices, questionnaires, documents and sources and the more objective data measured and collected by the certified AWA wellness technicians are combined with the objective internal laboratory Scientific Wellness analyses of selected body fluids, hair and the cardiovascular system; its blood chemistries, sugars and lipids; liver function; the lymphocytic immune system; and/or analyses of urine/sputum/hair chemistries. Special data gathering programs and devices have been designed for each major category to check the validity of the gathered data before it is transferred into the specific processing areas of the evaluation and quantifying programs. In order to insure the most accurate and meaningful evaluations, each of the data gathering and evaluation/quantification programs has been customized to meet the special needs of quantifying and analyzing the various types of data being processed. The evaluation/quantification programs compare and contrast the gathered data to all the corresponding gathered data areas as well as to the major evaluation and processing areas of the exclusive Scientific Wellness Data Base. Next, the evaluation programs process the data according to specific formuli and algorythmns and create an adjusted data output. The adjusted data outputs are fed to a series of customized output programs which generate special Output Reports that include both picturegraphic analyses and specific recommendations on a multiple-page printout of individualized recommendations for improving and/or maintaining specific measured wellness ranking levels on the 10-Point Scientific Wellness Scales. The output programs, also may utilize a wellness data bank in which is stored a multiplicity of recommendations designed to fit as many comparative combinations as possible of the different circumstances which are likely to be made reference to by the gathered adjusted input data. Specific items of information can be highlighted in the participant's individualized Output Report so that each of the important wellness rankings are graphically and easily understood when combined with the participant's multiple-page scientific wellness output report with recommendations and summary and at the same time relate personally to the participant's "assessed" wellness outlooks, behaviors, habits and lifestyle as well as to specifically "measured" physiological and "analyzed" laboratory data and information.

SCIENTIFIC WELLNESS HAS THREE (3) IMPORTANT MAJOR AREAS

The "Parameters" for Scientific Wellness, Optimal Health and Fitness fall into three major areas which can be tested "scientifically and objectively." These Three (3) Major Areas provide sufficient ranking or rating information to assist the individual in making optimally healthy decisions in all the important areas of outlooks and lifestyle choices.

The First group of Scientific Wellness Parameters are the "Assessed" Non-Physical Categories of Optimal Outlooks, Basic Attitudes, Behaviors and Health Habits. The Second group of Scientific Wellness Parameters are the "Measured" Optimal Physiological Parameters of Super-Health and Fitness. The Third set of Parameters are the "laboratory Analyzed" Hidden Inside Measurements of Comprehensive Blood Chemistries and Immune System Analyses.

Together, these Parameters comprise the Three (3) Cross-Correlated Major groups of Parameters of Optimal Health which objectively quantify a person's level of Scientific Wellness. In addition, they also evaluate one's present "Health Risk" Factors and serve as predictors and/or indicators of the earliest possible detection of potential serious sickness or disease.

FIGS. 3A–3K: THE NON-PHYSICAL PARAMETERS OF SCIENTIFIC WELLNESS

The Non-Physical Parameters of Scientific Wellness include: basic attitudes/outlooks, core beliefs, behaviors and commitment to wellness, plus mental and emotional balance and health, and, relationship(s)' wellness; eating and drinking habits, the use of natural foods, low-fat nutrition and dietary habits; regular gentle non-stressful aerobic activities and cardiovascular exercise; environmental/smoking habits; use of vitamins/minerals/herbs supplements and pure water; personal medical and immune histories; family medical and immune histories; major stress and risk evaluations; frequency and quantity of any medications used; and one's health and safety habits.

FIG. 3A is a reproduction of a portion of the typical individualized and personal Scientific Wellness multicolor visual depictions and analysis information showing the participant's ranking on this 10-Point Non-Physical Scientific Wellness Parameter categorized as the "Outlooks, Basic Attitudes and Behaviors Scale" combined with the highlighted suggestions and recommendations that are correlated to this specific summary evaluation 10-Point Scale Rating.

FIG. 3B is a reproduction of a portion of the typical individualized and personal Scientific Wellness multicolor visual depictions and analysis information showing the participant's ranking on this 10-Point Non-Physical Scientific Wellness Parameter categorized as the "Attitude and Commitment to Health and Fitness and Wellness Scale" combined with the highlighted suggestions and recommendations that are correlated to this specific summary evaluation 10-Point Scale Rating.

BASIC ATTITUDES, CORE BELIEFS (OUTLOOKS) AND BEHAVIORS AND COMMITMENT TO WELLNESS

Research has surprisingly demonstrated repeatedly that the most important categories for determining optimal wellness are those of basic attitudes, core beliefs (outlooks) and behaviors. These "basic attitudes, outlooks and behaviors" are foundational to all of the Parameters of "optimal wellness, health and fitness." These have turned out to be the most significant and important Parameters statistically, because out of this Parameter all of one's lifestyle habits and bottom line behaviors are determined, every last one of them, in fact, from what one does when s/he gets up in the morning to what s/he does before s/he finally retires at night and goes to bed for sleep.

Equally important is a person's commitment to his/her own personal wellness. These areas of "basic attitudes, core beliefs, behaviors and commitment to wellness" have been repeatedly found to be the "most important and significant factors" to measure in determining a person's level of wellness and optimal health.

Measuring and ranking these Parameters was originally not very easy; because the only instruments available to measure the basic attitudes, core beliefs, behaviors or commitment to wellness were generally non-validated batteries of health questionnaires, use of professional interviews and/or the standard (non-validated and therefore questionable) psychological tests. The results of individual psychological tests generally are determined by how a person feels that particular day and then ANSWERS the test questions. Because of this, they are virtually impossible to use for verifiable or validated results. The other frustrating component that made it difficult to ascertain these basic outlooks, attitudes, behaviors and commitment to wellness is the fact that there was no significant way to correlate or have these mental or psychological tests validated because, however a person wants to answer the question is how it is answered in that moment. There were no reliable ways to keep the person's answers/responses honest.

Research showed that people, with greater intelligence or perhaps photographic memories, could remember the different questions on a test, and that it became easier and easier for such individuals to actually answer the questions exactly the way they wanted to answer it; but not necessarily what was really the honest truth. Thus the standard psychological tests to measure these core beliefs and attitudes have not been very well documented and/or statistically validated instruments in the past. Even more important was the fact that no one had ever correlated the mental or psychological assessments to such objective physiological parameters or tests as: blood pressure or hypertension, or cholesterol levels, or triglycerides, or any of the major physiological parameters.

In the early Scientific Wellness research of these parameters of optimal health and wellness, a variety of new psychological tests and measurements had to be designed, developed and experimented with on a wide variety of populations to determine what were the optimal basic attitudes, behaviors, outlooks and core beliefs.

MENTAL AND EMOTIONAL HEALTH AND BALANCE

The next component Which is very important, in terms of quantifying and tracking wellness, is an individual's mental and emotional balance and health. This includes intellectual, emotional, and mental factors. These are the factors that are often the most difficult to assess or evaluate from a scientific perspective. The reason for this is that there are no standardized evaluation systems to determine what are the proper or "healthy" feelings or emotions. Generally, the professionals in the fields of psychiatry and/or psychology and/or marriage and family counseling feel or believe that "any emotion" is proper, so long as it is a true emotion and not a contrived or cover up emotion. But this theory or opinion of professionals had not been tested to any objective degree.

NURTURING/HEALTHY RELATIONSHIP(S)

Another Parameter that relates to the mental or emotional balance is that of nurturing/healthy relationships, which are very important in people's lives but often people have very little training in how to have good, top quality relationships. The Scientific Wellness assessments include these areas, evaluates and ranks them from an optimal perspective.

FIG. 3C is a reproduction of a portion of the typical individualized and personal Scientific Wellness multicolor visual depictions and analysis information showing the participant's ranking on this 10-Point Non-Physical Scientific Wellness Parameter categorized as the "Eating, and Drinking Habits Scale" combined with the highlighted suggestions and recommendations that are correlated to this specific summary evaluation 10-Point Scale Rating.

EATING/DRINKING HABITS OF NATURAL FOODS AND LOW-FAT DIET

Next, in the major optimal health Parameters, is the category of diet and nutrition. This is a factor that is often widely considered to be the most important of all for optimal health. Surprisingly and statistically, it has been found to be not as important as the first Parameters of basic attitudes, core beliefs (outlooks), behaviors and commitment to wellness. Basic nutrition, low-fat diet and the use of natural (non-processed or fast foods) foods, however, are some of the most important ingredients in achieving and/or maintaining a healthy immune system and optimal wellness, because they provide the basic building blocks for both wellness and longevity. Another important ingredient is the purity of drinking and cooking water.

Statistically, the diet and nutrition Parameter is an important one because it is the foundational system for all of the replacement ingredients to keep cells healthy, vibrant and functioning optimally in the body. It is the Parameter which determines the amount of fat in a person's diet and the amount of cholesterol type materials in the cardiovascular system as well as the amount of salts and sugars and other ingredients which can either bring a person to optimal health and wellness or cause them potential sickness and disease or other complications. This is a scientific approach to personal dietary nutritional needs and it comes from over twenty years of research on actually helping people determine the best diet for each person's unique metabolism, physiology and genetics.

FIG. 3D is a reproduction of a portion of the typical individualized and personal Scientific Wellness multicolor visual depictions and analysis information showing the participant's ranking on this 10-Point Non-Physical Scientific Wellness Parameter categorized as the "Physical Activity and Exercise Habits Scale" combined with the highlighted suggestions and recommendations that are correlated to this specific summary evaluation 10-Point Scale Rating.

REGULAR GENTLE NON-STRESSFUL MOVEMENT AND AEROBIC PHYSICAL ACTIVITIES

The fourth most important non-physical Parameter is regular gentle non-stressful aerobic activities and cardiovascular exercise. This is the third biggest factor and the most neglected in achievable levels of health and fitness. Most people in modern society live a sedentary life style. Most people on the job sit more than they move around. Consequently, many people have a need for adding gentle aerobic exercise into their daily lifestyle because they are not very active.

It is necessary to assess the amount of a person's regular gentle non-stressful aerobic activities and cardiovascular exercise in terms of measuring their wellness. Generally, research shows that most people can benefit from having additional amounts of gentle aerobic physical activity and exercise to help their entire cardiovascular system become more efficient.

How does exercise relate to one's cardiovascular efficiency? As the person exercises from a resting heart rate, the pulse increases to the level of a physical activity. As the heart rate goes up with the vigorousness of the activity, the heart pumps more blood throughout the body. More oxygen is also taken into the body by this process.

As the heart rate goes up to an aerobic level it strengthens the entire system. This means that when a person has been able to reach an exercise level that is 80% of one's target heart rate; that individual develops a much stronger cardiovascular system by doing an activity that brings them to an aerobic level of cardiovascular function on a regular basis, at least two or three times a week.

Over time, what happens to the cardiovascular system as a major muscular system, the arteries, all the muscles in and around the heart, and the heart muscle itself, as these muscles are used regularly they develop strength, they develop more efficient contraction levels and the heart becomes stronger and stronger in terms of stamina. As this happens, the resting heart rate, or the pulse, reduces.

Peak performing athletes have been known to have resting heart rates down into the thirties and forties beats per minute. The average person generally has a heart rate in the mid-seventies. The lower the resting heart rate, the more efficient the cardiovascular system. Regular "cardiovascular exercise" has become a very important factor in maintaining wellness.

FIG. 3E is a reproduction of a portion of the typical individualized and personal Scientific Wellness multicolor visual depictions and analysis information showing the participant's ranking on this 10-Point Non-Physical Scientific Wellness Parameter categorized as the "Smoking and Environmental Habits Scale" combined with the highlighted suggestions and recommendations that are correlated to this specific summary evaluation 10-Point Scale Rating.

SMOKING/ENVIRONMENTAL WELLNESS HABITS

The next important non-physical Parameters are the smoking habits, or being around smoke, and environmental habits, including both air and water. The purity of air and water are very important to achieving and maintaining optimal health and fitness. They are not as important as the basic attitudes or core beliefs or the diet and eating habits, or the cardiovascular exercise, but they are still important enough that they must be considered as a measurement of wellness.

FIG. 3F is a reproduction of a portion of the typical individualized and personal Scientific Wellness multicolor visual depictions and analysis information showing the participant's ranking on this 10-Point Non-Physical Scientific Wellness Parameter categorized as the "Health and Safety Habits Scale" combined with the highlighted suggestions and recommendations that are correlated to this specific summary evaluation 10-Point Scale Rating.

HEALTH AND SAFETY HABITS

The next category that is measured in terms of non-physical Parameters is that of a person's health and safety habits. These include: the amount of sleep one gets, how regularly it is gotten, and the quality of that sleep. Other safety habits, like wearing seat belts or helmets are important when operating a motor vehicle, when traveling on a bike or motorcycle; as well as other safety habits.

FIG. 3G is a reproduction of a portion of the typical individualized and personal Scientific Wellness multicolor visual depictions and analysis information showing the participant's ranking on this 10-Point Non-Physical Scientific Wellness Parameter categorized as the "Herbs, Minerals, Vitamins and Nutritional Supplements Habits Scale" combined with the highlighted suggestions and recommendations that are correlated to this specific summary evaluation 10-Point Scale Rating.

USE OF HERBS, MINERALS, VITAMINS AND NUTRITIONAL/FOODS SUPPLEMENTS

Another major optimal health Parameter is the category of herbs, minerals, vitamins and other nutritional foods or supplements. This is a category that has become more and more important as the nutritional ingredients and quality of mass produced super-market foods and produce has dramatically deteriorated. Research, even by governmental agencies, has demonstrated the average person's need for adding herbs, minerals, vitamins and other nutritional foods or supplements to one's diet. Basic nutrition supported by dietary supplements and natural (non-processed or fast foods), foods can provide all of the important ingredients needed for achieving and/or maintaining optimal wellness.

FIG. 3H is a reproduction of a portion of the typical individualized and personal Scientific Wellness multicolor visual depictions and analysis information showing the participant's ranking on this 10-Point Non-Physical Scientific Wellness Parameter categorized as the "Use of Medications, Substances and Prescription Drugs Habits Scale" combined with the highlighted suggestions and recommendations that are correlated to this specific summary evaluation 10-Point Scale Rating.

USE OF MEDICATIONS, SUBSTANCES AND PRESCRIPTION DRUGS

In a modern world where there are innumerable ads for substances and coping mechanisms, it is important to evaluate a person's frequency and quantity of any medications, substances or prescription drugs used. Core attitudes and beliefs, outlooks and behaviors can be altered by the frequent use of any mind altering medications, substances or drugs. To the wellness researcher, the use of these items must be known in order to fully evaluate a participant's potential for wellness.

FIG. 3I is a reproduction of a portion of the typical individualized and personal Scientific Wellness multicolor visual depictions and analysis information showing the participant's ranking on this 10-Point Non-Physical Scientific Wellness Parameter categorized as the "Personal Medical, Health and Fitness Histories Scale" combined with the highlighted suggestions and recommendations that are correlated to this specific summary evaluation 10-Point Scale Rating.

PERSONAL MEDICAL, HEALTH AND FITNESS HISTORIES

The next category of investigation is one's personal medical, health and fitness histories and experiences up to this point in their life. These factors may determine achievable levels of wellness and optimal health or fitness, because they may cause severe limitations that cannot be ignored. Even with the healthiest outlooks and most nutritional diet, previous surgeries, heart disease, cancers, immune disorders or other severe diseases may limit future levels of personal wellness.

FIG. 3J is a reproduction of a portion of the typical individualized and personal Scientific Wellness multicolor visual depictions and analysis information showing the participant's ranking on this 10-Point Non-Physical Scientific Wellness Parameter categorized as the "Family Medical and Immune Histories Scale" combined with the highlighted suggestions and recommendations that are correlated to this specific summary evaluation 10-Point Scale Rating.

FAMILY MEDICAL AND IMMUNE HISTORIES

Genetics is another factor that cannot be ignored in ascertaining achievable levels of wellness and optimal health or fitness, because these may introduce some limitations. Wellness researchers have discovered that these factors have been over played in importance, mostly because genetic research never considered inherited behaviors and habits in their investigations. But genetic predispositions, strengths and weaknessess cannot be ignored in determining potential levels of optimal health, fitness or wellness. Therefore, it is important to assess one's family medical and immune histories.

FIG. 3K is a reproduction of a portion of the typical individualized and personal Scientific Wellness multicolor visual depictions and analysis information showing the participant's ranking on this 10-Point Non-Physical Scientific Wellness Parameter categorized as the "Personal Immune History Scale" combined with the highlighted suggestions and recommendations that are correlated to this specific summary evaluation 10-Point Scale Rating.

PERSONAL IMMUNE HISTORY

An increasingly important category of investigation is one's personal immune medical history and experiences up to this point in their life. These factors may affect achievable levels of wellness and optimal health or fitness, because they may cause some limitations that must be considered as challenges to achieving and/or maintaining optimal health and fitness. As chronic fatigue, hepatitis and AIDS reach out and touch more and more people, immune disorders and immunodeficiency conditions of the past may provide limitations to future levels of personal wellness.

FIGS. 4A–4J: PHYSIOLOGICAL CLINICAL MEASUREMENTS OF WELLNESS

Of equal and perhaps greater importance than all the non-physical Parameters above, are the major important Physiological Categories for simply and accurately measuring a person's level of wellness. These are the physiological tests and measurements that no one can cheat on. The previous Parameters of non-physical categories, such as attitudes, outlooks, behaviors, commitment to wellness, eating habits, exercise, personal medical, health, fitness and immune histories, family medical history, stressors, and use of substances are highly dependent upon a person's truthfulness and/or accuracy in filling out forms, questionnaires or document stating that their attitudes, outlooks, habits and behaviors are such, or their commitment to wellness is this, or that s/he is eating certain foods and exercising regularly, or that no substances are being used, when, in fact, maybe the truth is different than indicated in the responses. But no one can quickly change, cheat on the measurements or fool these physiological Parameters.

PHYSIOLOGICAL TESTS ASSURE GREATER ACCURACY OF OTHER PARAMETERS

The most innovative aspect of these state-of-the-art Scientific Wellness Tests and Measurements is that all of the Non-Physical Parameters have been cross-correlated over the last quarter century of research to these more accurate physiological Parameters. In the process of mathematically evaluating such cross-correlations for any statistical significance, an interesting phenomena was discovered. When a person filled out a form, questionnaire or document and told the computer about their attitudes, outlooks, commitment to wellness, eating habits, how often they exercised or how vigorously they exercised, their use of substances; the accuracy of their responses was magically increased to near perfect truth telling if that person was aware that their blood lipids (cholesterol, HDL, LDL, triglycerides) or glucose, or their resting heart rate, or their blood pressures would be measured, or a body fat measurement, or a stress temperature dot assessment was going to be taken by a technician within 48 hours. When the individual knew such measurements were certain, they became extremely honest, told the bottom line truth (even if damaging to their health image) on what their eating habits and attitudes were and the truth about whether or not they exercised, with what intensity, how regular and how much. This was not generally the case if the person only responded to the wellness data gathering forms, devices, questionnaires or documents by themselves.

NO ONE CAN CHEAT ON THESE PHYSIOLOGICAL MEASUREMENTS

Regularly utilizing these "Physiological Parameters" is probably the most important part of measuring wellness, because nobody can "cheat" on them. People can't cheat on their blood pressure, their pulse rate, their stress temperature, or how fat they are. Because of this, these simple measurements guarantee a much greater accuracy on the evaluation of both the psychological and the lifestyle Parameters (habits) than was ever achievable before these cross-correlations were discovered, documented, verified and validated.

This means that the physical tests and measurements are some of the "most important" Parameters for measuring wellness, viz., the resting and exercise heart rates, the recovery heart rates, the oxygen utilization, the blood pressure measurements, the body fat composition (the percentage of fat to muscle), the circulation efficiency stress temperature measurement (especially at the extremities), the height and weight ratio, the type of frame, urine and saliva (sputum) analyses, blood cell analyses, and the vital capacity pulmonary function and the forced expiratory volume (for smokers).

OBJECTIVE PHYSICAL TESTS USEFUL FOR MONITORING WELLNESS

These physiological tests and measurements are vitally important to determine one's level of optimal health and fitness at any time. All of these are ranked on a scale from one to ten. The combination of these tests and measurements objectively determine a person's true level of wellness. Fortunately, these measurements can be repeated periodically to determine any improvement(s) that one may be making as s/he decides to go for higher levels of Wellness.

BLOOD PRESSURE(S) TESTS FOR WELLNESS

A most common but very important measurement, which is also an indicator of the efficiency of the cardiovascular system, are the blood pressure(s). In blood pressure measurements, two different Parameters, the systolic and diastolic are tested.

FIG. 4A is a reproduction of a portion of the typical individualized and personal Scientific Wellness multicolor visual depictions and analysis information showing the participant's ranking on this 10-Point Physiological Scientific Wellness Parameter categorized as the "Systolic Blood Pressure Scale" combined with the highlighted suggestions and recommendations that are correlated to this specific summary evaluation 10-Point Scale Rating.

THE SITUATIONAL SYSTOLIC BLOOD PRESSURE

The Systolic blood pressure is very situational. A person can travel on a freeway, can have some major stress or have something happen suddenly to frighten them, and their Systolic will go up noticeably. It is dramatically affected by a variety of stressful circumstances. The Systolic is the pressure that is measured when the heart is contracting and pumping blood throughout the system. So it is the highest number; it is the first figure one sees when a blood pressure reading is taken by a technician.

FIG. 4B is a reproduction of a portion of the typical individualized and personal Scientific Wellness multicolor visual depictions and analysis information showing the participant's ranking on this 10-Point Physiological Scientific Wellness Parameter categorized as the "Diastolic Blood Pressure Scale" combined with the highlighted suggestions and recommendations that are correlated to this specific summary evaluation 10-Point Scale Rating.

THE NON-SITUATIONAL DIASYSTOLIC BLOOD PRESSURE

The Diastolic is not as situational as the Systolic. The Diastolic, which is the pressure measurement within the heart itself, and within the arteries and veins when the heart is between cycles as well as throughout the entire cardiovascular system when the system is at rest or not pumping, is determined by a number of factors. Some of these include: overall stress, the buildup of cholesterol in the blood vessels, arterial sclerotic conditions in the arteries, or in the heart itself, the efficiency and stamina of the heart muscle itself, or any other complications in terms of the complete internal cardiovascular system. All of these effect the Diastolic pressure, so it is the most important measurement in terms of achievable levels of wellness, because it is not very situational. The Diastolic test generally reveals the efficiency of the entire cardiovascular system. The Diastolic is primarily determined by the subject's level of health, fitness and wellness. When wellness scientists evaluate the risk levels represented in the blood pressure measurement(s), they consider both the Systolic (the pressure measurement) and the Diastolic. But for determining an individual's optimal wellness levels, it is the Diastolic that is much more important. This is true because it tells how one has really been living their life and the habits which they have developed over time.

FIG. 4C is a reproduction of a portion of the typical individualized and personal Scientific Wellness multicolor visual depictions and analysis information showing the participant's ranking on this 10-Point Physiological Scientific Wellness Parameter categorized as the "Resting Heart Rate Scale" combined with the highlighted suggestions and recommendations that are correlated to this specific summary evaluation 10-Point Scale Rating.

RESTING, ACTIVITY AND RECOVERY (PULSE) HEART RATES

Different heart rates are determined by the number of times per minute that the heart makes a contraction and pumps blood through the arteries of the cardiovascular system. There are three (3) types of fitness heart rates (resting, exercise, and recovery) that can be measured. The resting rate is the most important number to assess for wellness because that is the number of pulses per minute when a person is actually sedentary or lying down. The sedentary pulse or resting heart rate indicates a person's overall total-body cardiovascular efficiency and stress levels.

BEATS PER MINUTE SHOW LEVEL OF WELLNESS

The number of beats per minute in a resting heart rate will give an indication of the person's level of optimal health and fitness. It will also indicate what their level of condition is. It may be important to also know the exercise heart rate. This is often adjusted based on an individual's age and level of condition. If a person is really in good shape, then s/he can raise that exercise heart rate to a higher endurance level than one who has not exercised in many years and is willing to begin exercising. There is an appropriate target percentage for the exercise heart rates (80%) that is generally the ideal target rate for everyone whether involved in an improvement program or in a maintenance program based on their level of exercise ability and the age they are at this present time.

Wellness researchers have looked with a great deal of interest at the speed with which a person's exercise heart rate returns to the resting rate after that person has been exercising vigorously. This is called a recovery heart rate. It indicates how fast the cardiovascular system and the heart are able to return back the resting pulse rate after vigorous exercise. Because the resting pulse is ultimately affected by the average exercise and recovery heart rates, it is the only wellness measurement that is generally measured and tracked to indicate the efficiency of the entire cardiovascular system.

FIG. 4D is a reproduction of a portion of the typical individualized and personal Scientific Wellness multicolor visual depictions and analysis information showing the participant's ranking on this 10-Point Physiological Scientific Wellness Parameter categorized as the "Stress Measurement Scale" combined with the highlighted suggestions and recommendations that are correlated to this specific summary evaluation 10-Point Scale Rating.

STRESS AND RISK EVALUATIONS

Another component that has proven valuable to wellness scientists in quantifying wellness are assessments of major stress and risks. Though no objective system of determining total inner stress exists at this time, an evaluation of the areas and types of stressors and risks in a person's life are important. Even though stress still has a lot of unknown components and factors, its effects will still dramatically correlate to certain physiological and laboratory tested Parameters of wellness. Stress may affect such physiological scores as: stress temperatures, blood pressures and resting heart rates. It also changes internal numbers, including: major blood lipids, immunocompetancy of white blood cells, etc.

CIRCULATION EFFICIENCY/STRESS DOT TEMPERATURE TEST

The next most important health/fitness physiological assessment Parameter to get an idea of how healthy one is internally, is the circulation efficiency/stress dot temperature test at the extremities. This may include things like cold feet, cold hands, or things like that, and there are ways to measure how good a person's cardiovascular system is functioning to bring the blood all the way out to the extremities. This is an another important wellness measurement. It generally indicates the tension within one's body and how "chronic" or how tight certain muscle groups may be, whether or not they can be relaxed and let go; and if so, how fast.

FIG. 4E is a reproduction of a portion of the typical individualized and personal Scientific Wellness multicolor visual depictions and analysis information showing the participant's ranking on this 10-Point Physiological Scientific Wellness Parameter categorized as the "Body (Fat) Composition Scale" combined with the highlighted suggestions and recommendations that are correlated to this specific summary evaluation 10-Point Scale Rating.

BODY FAT PERCENTAGE MORE IMPORTANT THAN WEIGHT

The next really important measurement is body (fat) composition. This is a measurement where technicians actually measure the percentage of fat in the body fight under the skin. This is best done (for accuracy) by a wellness trained and certified technician with high-quality calipers. The caliper measurement, if done by a highly qualified technician will generally get as close as 97% accuracy on subcutaneous fat measurements. It is probably one of the easiest measurement to do. There is one other validated measuring system that is accurate (other than with the calipers) which can be done to measure this fat composition. It is the hydrostatic or underwater weighing, and is considered to be the most accurate, but it also takes the most time and is the most costly.

Measuring body fat is important in terms of wellness because this is an indicator of the level of wellness throughout the entire body. It is a measurement to determine the wellness of one's body because the greater amount of fat in the body the less likely an individual will have a long life and the greater the chances for various disorders usually related to obesity and to other health problems. Body fat is an extremely important measurement because it measures the percentage of fat to muscle tissue throughout the body.

Research has shown that weight alone is not as significant as the ratio of muscle to body fat. The ideal body fat percentages is different for women than for men. Wellness ideals are based on many years of research and testing many thousands of people to determine their ideal body fat percentage. For men, it is around 9–11%; but for women, it is 15–22%. Healthy women need more body fat than men because it is necessary for proper functioning of the delicate balances of their hormonal systems. These optimal percentages are based on many years of research and are used for determining not only a person's ideal weight but many other conditions that prevent sickness and disease and give quality of life to the individual.

Body fat serves another "psychological type of purpose" for some people since as they add more body fat it becomes an insulator to keep them from actually feeling things in their life or it serves to keep others at a distance. For this reason, psychologically speaking, the body fat measurement is a good indicator of a person's level of fear of closeness and their need for protection.

FIG. 4F is a reproduction of a portion of the typical individualized and personal Scientific Wellness multicolor visual depictions and analysis information showing the participant's ranking on this 10-Point Physiological Scientific Wellness Parameter categorized as the "Height and Weight Ratio Scale" combined with the highlighted suggestions and recommendations that are correlated to this specific summary evaluation 10-Point Scale Rating.

HEIGHT AND WEIGHT RATIO

The wellness physiological fat measurement ultimately determines the height and weight ratio. Calculating this may provide a simple, easy approximate measurement of body (fat) composition, if wellness trained and certified technicians are not available for accurate assessments of this important physiological wellness parameter. The calculation of a person's ideal height to weight ratio adjusts for different types of body frames, such as: small, medium or large (bones and body sizes).

FIG. 4G is a reproduction of a portion of the typical individualized and personal Scientific Wellness multicolor visual depictions and analysis information showing the participant's ranking on this 10-Point Physiological Scientific Wellness Parameter categorized as the "Urine Analyses Scale" combined with the highlighted suggestions and recommendations that are correlated to this specific summary evaluation 10-Point Scale Rating.

URINE ANALYSES

Quick clinical evaluations of the pH, sugars and color of a person's urine provide additional important optimal wellness Parameters that need to be periodically measured and tracked. Urine comes from the excretory system, and its pH, sugars and color reflect the overall health and wellness of the person. Monitoring this Parameter will indicate still another assessment of a person's level of wellness.

FIG. 4H is a reproduction of a portion of the typical individualized and personal Scientific Wellness multicolor visual depictions and analysis information showing the participant's ranking on this 10-Point Physiological Scientific Wellness Parameter categorized as the "Saliva (Sputum) Analyses Scale" combined with the highlighted suggestions and recommendations that are correlated to this specific summary evaluation 10-Point Scale Rating.

SALIVA (SPUTUM) ANALYSES

Clinical evaluations of the pH of a person's saliva provide other information that needs to be monitored and evaluated. Saliva is produced from glands in the mouth and is an indicator of the health and wellness of the person. Monitoring this Parameter will indicate still another measurement of a person's level of wellness.

FIG. 4I is a reproduction of a portion of the typical individualized and personal Scientific Wellness multicolor visual depictions and analysis information showing the participant's ranking on this 10-Point Physiological Scientific Wellness Parameter categorized as the "Blood Cells Analyses Scale" combined with the highlighted suggestions and recommendations that are correlated to this specific summary evaluation 10-Point Scale Rating.

BLOOD CELLS ANALYSES

Simple blood evaluations will measure and track other indicators of a person's level of optimal health, fitness and wellness. Clinical observation of this information results in important data that needs to be monitored and tracked for improvements. Blood is the vital fluid that circulates throughout the body. A careful observation of its ingredients may provide indicators of the health and wellness of a person. Observing this Parameter will indicate still another evaluation of a person's level of wellness.

FIG. 4J is a reproduction of a portion of the typical individualized and personal Scientific Wellness multicolor visual depictions and analysis information showing the participant's ranking on this 10-Point Physiological Scientific Wellness Parameter categorized as the "Lung Vital Capacity/Forced Volume Evaluation Scale" combined with the highlighted suggestions and recommendations that are correlated to this specific summary evaluation 10-Point Scale Rating.

LUNG VITAL CAPACITY/FORCED VOLUME EVALUATION

Evaluations of a person's Lung Vital Capacity/Forced Volume provide added important information, especially for individuals that work or live in a very smoggy area or have smoked excessively in the past (but quit) or for those that are still smoking or living with a smoker. The assessment of this Parameter is generally optional for non-smokers or for those who work or live in non-smoggy areas. But for individuals who are smoking or exposed to heavy smoke or smog these need to be evaluated and tracked. The vital capacity and forced volume of the lungs are important indicators of the optimal health and wellness of the person. Monitoring this Parameter will indicate still another measurement of a person's level of wellness.

FIGS. 5A–5L LABORATORY BIOCHEMICAL BLOOD ANALYSES OF WELLNESS

Even more important than the physiological Parameters of health and fitness are the Biochemical Categories of optimal wellness. Again, these can be assessed through standard laboratory analyses of blood, urine and/or hair. These biochemical measurements must of necessity be done through medical testing laboratories. The actual samples for the test can be taken anywhere. These are generally found in a comprehensive SMAC 24 blood chemistry analyses and/or a comprehensive immunocytotoxic evaluation. A trained lab technician, usually known as a phlebotomist, draws the blood from a person for analyses by a qualified laboratory.

BLOOD LIPIDS DETERMINE INTERNAL HIDDEN LEVELS OF WELLNESS

In these analyses, a careful evaluation is performed on the following Parameters: total cholesterol, high density lipoproteins, low density lipoproteins, triglycerides, glucose, sugars, proteins, vitamins, and minerals. In an analysis of these ingredients, the primary concern is with the ones which relate to the most important areas of wellness. These Blood Lipids include: Total Cholesterol, High-Density Lipoproteins (HDLs), Low-Density Lipoproteins (LDLs), and the Triglycerides.

All the other ingredients are important but are not necessarily related to the most important areas of wellness and do not relate to the number one and two major diseases or mortality factors. It is primarily the Cholesterol, Triglycerides, LDLs and the HDLs relationships that determine one's optimal health or high risk levels. Research has shown that Cholesterol alone is not a very significant number. Much more important than one's level of Total Cholesterol are the ratios of Cholesterol to HDL and LDL to HDL that significantly correlate to cardiovascular health or disease. Thus, one of the most important laboratory measurements is a Cholesterol to HDL ratio. Furthermore, the LDL Score must be kept under 120 to maintain a Low-Risk Level. The LDL to HDL Ratio is also a very important indicator of both wellness and risk levels. The Triglycerides, too, are important because as lipids they determine a major portion of the overall risks of cardiovascular disfunction and contribute to the LDLs.

FIG. 5A is a reproduction of a portion of the typical individualized and personal Scientific Wellness multicolor visual depictions and analysis information showing the participant's ranking on the first 10-Point Physiological Scientific Wellness Parameter categorized as the "Blood Glucose Analysis Scale" combined with the highlighted suggestions and recommendations that are correlated to this specific summary evaluation 10-Point Scale Rating.

BLOOD GLUCOSE ANALYSIS

Blood Glucose Level is an important Parameter to be evaluated to determine one's Scientific Wellness Levels. This measurement indicates potential hypoglycemic or diabetic conditions and is an important value for monitoring achievable levels of optimal wellness, health and fitness.

FIG. 5B is a reproduction of a portion of the typical individualized and personal Scientific Wellness multicolor visual depictions and analysis information showing the participant's ranking on the first 10-Point Scientific Physiological Wellness Parameter categorized as the "Blood Liver Analysis Scale" combined with the highlighted suggestions and recommendations that are correlated to this specific summary evaluation 10-Point Scale Rating.

BLOOD LIVER ANALYSIS

Blood Liver Analysis is another important Parameter for measuring a person's Optimal Levels of Scientific Wellness. This Parameter indicates the health or dysfunctional levels of the Liver and is useful in tracking alcohol abuses and monitoring achievable levels of optimal wellness, health and fitness.

FIG. 5C is a reproduction of a portion of the typical individualized and personal Scientific Wellness multicolor visual depictions and analysis information showing a person's ranking on the first 10-Point Physiological Scientific Wellness Parameter categorized as the "Total Blood Triglycerides Analysis Scale" combined with the highlighted suggestions and recommendations that are correlated to this specific summary evaluation 10-Point Scale Rating.

TOTAL BLOOD TRIGLYCERIDES (LIPIDS)

Blood Triglycerides (Lipids) are a very important factor in the assessing a persons Scientific Wellness Levels as a combination of both objective and subjective data. These blood Triglycerides are especially important lipids for evaluating and calculating the amount of low density lipids (LDLs) in the blood stream and in monitoring achievable levels of optimal wellness, health and fitness.

FIG. 5D is a reproduction of a portion of the typical individualized and personal Scientific Wellness multicolor visual depictions and analysis information showing the participant's ranking on the first 10-Point Scientific Physiological Wellness Parameter categorized as the "Total Blood Cholesterol Analysis Scale" combined with the highlighted suggestions and recommendations that are correlated to this specific summary evaluation 10-Point Scale Rating.

TOTAL BLOOD CHOLESTEROL ANALYSIS

Scientific research on Total Blood Cholesterol (Lipids) has shown the importance of the Personal Scientific Wellness Evaluation System based on the validated 10-Point Scientific Wellness Scales. Most people are aware of the dangers of ultra-high levels of cholesterol. Thus this Score is vital in measuring levels of stress and tracking achievable levels of optimal wellness, health and fitness. Its relation to other lipids (HDLs) is important to assess.

FIG. 5E is a reproduction of a portion of the typical individualized and personal Scientific Wellness multicolor visual depictions and analysis information showing the participant's ranking on the first 10-Point Physiological Scientific Wellness Parameter categorized as the "Total Blood HDLs Analysis Scale" combined with the highlighted suggestions and recommendations that are correlated to this specific summary evaluation 10-Point Scale Rating.

TOTAL BLOOD HDLS (HIGH-DENSITY LIPIDS)

Total Blood HDLs (High-Density Lipids) are very important factors in the evaluation of a person's Scientific Wellness Levels. These blood low-density lipids are especially important for evaluating and/or calculating the amounts of the dangerous low-density lipids (LDLs) in the blood stream. HDLs are the most desirable type of blood lipids, therefore this Score is a very important item in evaluating achievable levels of optimal wellness, health and fitness.

FIG. 5F is a reproduction of a portion of the typical individualized and personal Scientific Wellness multicolor visual depictions and analysis information showing the participant's ranking on the first 10-Point Physiological Scientific Wellness Parameter categorized as the "Total Cholesterol to HDL Ratio Scale" combined with the highlighted suggestions and recommendations that are correlated to this specific summary evaluation 10-Point Scale Rating.

TOTAL CHOLESTEROL TO HDL RATIO

Total Cholesterol to HDL Ratio is a very important Parameter in the evaluation of a person's Scientific Wellness Levels. This Ratio is especially important for evaluating and/or calculating the risk of heart or cardiovascular disease and the amount of the most dangerous lipids (the LDLs) in the blood stream. Research has demonstrated that this Ratio is one of the most important numbers to know in predicting and preventing cardiovascular diseases. It is also a vital measurement in monitoring achievable levels of optimal wellness, health and fitness.

FIG. 5G is a reproduction of a portion of the typical individualized and personal Scientific Wellness multicolor visual depictions and analysis information showing the participant's ranking on the first 10-Point Physiological Scientific Wellness Parameter categorized as the "Total LDL to HDL Ratio Scale" combined with the highlighted suggestions and recommendations that are correlated to this specific summary evaluation 10-Point Scale Rating.

TOTAL LDL TO HDL RATIO

Total LDL to HDL Ratio is another one of the most important Parameters in the assessment of a person's Scientific Wellness Levels. This Ratio is exceedingly important for evaluating and/or calculating major risk levels of heart and/or cardiovascular disease and the number of LDLs (the dangerous type that cause occlusions) present in the blood stream. This Ratio is also one of the most important numbers to evaluate in predicting and preventing cardiovascular diseases. It is also a necessary measurement in assessing and tracking achievable levels of optimal wellness, health and fitness.

FIG. 5H is a reproduction of a portion of the typical individualized and personal Scientific Wellness multicolor visual depictions and analysis information showing the participant's ranking on the first 10-Point Physiological Scientific Wellness Parameter categorized as the "Total Immunocompetency Evaluation Scale" combined with the highlighted-suggestions and recommendations that are correlated to this specific summary evaluation 10-Point Scale Rating.

TOTAL IMMUNOCOMPETENCY EVALUATION

Because of modern immune disorders, Total Immunocompetency Evaluation has become another one of the most important Parameters in the evaluation of a person's Scientific Wellness Levels. This Category is exceedingly important for evaluating and/or calculating major risk levels of immune disorders or disease. This Parameter is also one of the most important numbers to evaluate in predicting and preventing cancers, tumors or AIDS. It is also a necessary measurement in assessing and tracking achievable levels of optimal wellness, health and fitness.

FIG. 5I is a reproduction of a portion of the typical individualized and personal Scientific Wellness multicolor visual depictions and analysis information showing the participant's ranking on the first 10-Point Physiological Scientific Wellness Parameter categorized as the "Total Immune System Natural Killer Cell (NK) Activity Evaluation Scale" combined with the highlighted suggestions and recommendations that are correlated to this specific summary evaluation 10-Point Scale Rating.

TOTAL IMMUNE SYSTEM NK ACTIVITY EVALUATION

The potential of AIDS and other immune disorders can now be measured and tracked with a comprehensive immune system test, the Total Immune System NK Activity Evaluation. It may be one of the most important Parameters to assess in the quantification of a person's Scientific Wellness Levels. This category is exceedingly important in the determination of major risk levels of either immune disorders or disease. This Parameter is definitely one of the most important numbers to evaluate in predicting and preventing AIDS, tumors or cancers. This test is a new technology added recently to the Scientific Wellness Scales because it provides accurate values for evaluating and quantifying the health and virility of the immune system as well as providing early detection of immune disorders or dysfunctions and quantifying and tracking achievable levels of optimal wellness, health and fitness.

FIG. 5J is a reproduction of a portion of the typical individualized and personal Scientific Wellness multicolor visual depictions and analysis information showing the participant's ranking on the first 10-Point Physiological Scientific Wellness Parameter categorized as the "Total Immune System Vitality and NKHT3% Evaluation Scale" combined with the highlighted suggestions and recommendations that are correlated to this specific summary evaluation 10-Point Scale Rating.

TOTAL IMMUNE SYSTEM VITALITY AND NKHT3% EVALUATION

In quantifying the Immune System in relation to wellness and optimal health, the Total Immune Vitality and NKHT3% Evaluation must be evaluated. It is one Parameter that assesses the vitality of a person's Immune System and their Scientific Wellness Levels. This Category is exceedingly important in the determination of both optimal immune system functioning and major risk levels of immune disorders and/or disease. This test is a new technology added recently to the Scientific Wellness Scales because it provides accurate data and is important in monitoring, predicting and preventing immune disorders of any kind. It is also a vital measurement in evaluating and tracking achievable levels of optimal wellness, health and fitness.

FIG. 5K is a reproduction of a portion of the typical individualized and personal Scientific Wellness multicolor visual depictions and analysis information showing the participant's ranking on the first 10-Point Physiological Scientific Wellness Parameter categorized as the "Total Autoimmunology NK, B, and T-Cell Counts Evaluation Scale" combined with the highlighted suggestions and recommendations that are correlated to this specific summary evaluation 10-Point Scale Rating.

TOTAL AUTOIMMUNOLOGY NK, B, ABD T-CELL COUNTS EVALUATION

The overall wellness levels of the Immune System can now be tested, quantified and tracked with a comprehensive immune system test that includes an evaluation and count of Autoimmunology NK, B, and T-Cell Counts. This Category is important in the evaluation of major risk levels of either immune disorders or disease. This Parameter is definitely one of the important factors to track as one's Immune System improves. This test is a new technology added recently to the Scientific Wellness Scales because it provides accurate data for evaluating and quantifying the health and virility of the Total Immune System as well as providing early detection of either immune disorders or dysfunctions and quantifying and tracking achievable levels of optimal wellness, health and fitness.

FIG. 5L is a reproduction of a portion of the typical individualized and personal Scientific Wellness multicolor visual depictions and analysis information showing the participant's ranking on the first 10-Point Physiological Scientific Wellness Parameter categorized as the "Immune T-Cell Helper/Suppressor Ratio Evaluation Scale" combined with the highlighted suggestions and recommendations that are correlated to this specific summary evaluation 10-Point Scale Rating.

IMMUNE T-CELL HELPER/SUPPRESSOR RATIO EVALUATION

One of the most important functions of the Immune System is the balance and wellness of the T-Cell Helper/Suppressor Ratio. This factor has become one of the most important Parameters in evaluating of a person's Scientific Wellness Levels. This category is vital and important for assessing and/or monitoring major risk levels of immune disorders or disease. This Parameter is a very important numbers to assess in predicting and preventing cancers. It is also a necessary measurement in assessing and tracking achievable levels of optimal wellness, health and fitness.

FIG. 6 is a reproduction of a portion of the individualized personal Scientific Wellness multicolor summary evaluation and rating chart that graphically depicts on one page all of the ranking validated 10-Point Scientific Wellness Scales included in a report. This chart gives a summary view of the entire report. It provides the person participating in the Scientific Wellness assessments a graphically depicted overview of all the Scientific Wellness tests and measurements included in the Output Report.

FIG. 7 is a reproduction of a portion of the ranking chart with score ranges and the adjusted ranking factors for the "Insurability Ranking Factors for Non-Physical Assessments Scales" for the Personal Scientific Wellness Evaluation Rating Scales based on the quantified and validated 10-Point Scientific Wellness Scales. Utilizing the Insurability Ranking Factors related to the Non-Physical Parameters of wellness, mathematicians can adjust for graduated premiums and deductibles in accordance with the ranking factors for quantified wellness and risk levels.

FIG. 8 is a reproduction of a portion of the ranking chart with score ranges and the adjusted ranking factors for the "Insurability Ranking Factors for Physiological Clinical Tests and Measurements" for the Personal Scientific Wellness Evaluation Rating Scales based on the quantified and validated 10-Point Scientific Wellness Scales. These Insurability Ranking Factors, related to Objective Physiological Parameters of wellness, provide actuaries and mathematicians with a graduated adjustment scale for determining a system of graduated premiums and deductibles in accordance with the ranking factors for quantified wellness and risk levels.

FIG. 9 is a reproduction of a portion of the ranking chart with score ranges and the adjusted ranking factors for the "Insurability Ranking Factors for Laboratory Analyses" for the Personal Scientific Wellness Evaluation Rating Scales based on the quantified and validated 10-Point Scientific Wellness Scales. The laboratory rankings coupled with their Insurability Ranking Factors offer one of the most accurate and scientifically objective systems for using the Parameters of wellness to calculate actuarially the appropriate adjustment scales for determining a system of graduated premiums and deductibles in accordance with the ranking factors for quantified wellness and risk levels.

The invention thus sets forth a comprehensive wellness scheme which, if followed by an individual, should result in a longer, optimally healthy and more fulfilling life. Various changes can be made to the invention without departing from the spirit thereof or scope of the following claims.

What is claimed is:

1. A method of preparing a personal analysis for an individual using information gathered from the individual and a previously created scientific wellness and health risk database, the method comprising the steps of
   a. establishing a list of measurable categories of wellness, health, fitness and risk-related information,
   b. creating a data gathering scheme for each said category,
   c. utilizing the scheme to gather subjective and objective data on the individual,
   d. compiling the data, checking the data for validity, and storing the validated data as an inventory of wellness, health, fitness and risk-related knowledge, and
   e. preparing an evaluation of said knowledge by comparing said knowledge with said database to create a report having two parts, a first part having a series of visual depictions each having analysis information categorized as:
      i. excellent well-being, also known as extremely low risk,
      ii. good well-being, also known as low risk,
      iii. average well-being, also known as average risk
      iv. poor well-being, also known as high risk
      v. dangerous well-being, also known as extremely high risk
   and a second part comprising a series individualized evaluations and recommendations for improvement, each of said second part being printed proximate a selected one of said first part for review in combination with said one of said first part.

2. The method according to claim 1 including establishing one of said categories as assessed quantifiable parameters comprising
   i. outlooks, basic attitudes and self-love,
   ii. eating and drinking habits,
   iii. physical activity and exercise habits,
   iv. alcohol, medication, supplements, smoking and drug consumption,
   v. environment, health and safety behaviors,
   vi. personal and family physical, genetic and medical histories,
   vii. stress/distress, and
   viii. healthy (nurturing) relationships
said categories comprising subjective non-physical parameters of scientific wellness, optimal health and fitness and medical risk.

3. The method according to claim 1 including establishing one of said categories as measured quantifiable parameters comprising
   i. resting heart rate,
   ii. blood pressure,
   iii. body composition,
   iv. height and weight ratio, and
   v. stress/distress
said categories comprising objective physiological measurements of scientific wellness, optimal health and fitness and medical risk.

4. The method according to claim 1 including establishing one of said categories as analyzed quantifiable parameters comprising
   i. blood chemistries
   ii. urine,
   iii. lipids, and
   iv. immune system,
said categories comprising objective laboratory parameters of scientific wellness, optimal health and fitness and medical risk.

5. The method according to claim 1 including in method step "e" preparing said evaluation in the form of at least one visually accented graph, each graph having an associated report.

6. The method according to claim 5 in which said graph has a graduated 10-point scale.

7. The method according to claim 6 in which each two points of said 10-point scale depict one of said visual depictions.

8. A method for assessing, measuring, quantifying, evaluating, validating, correlating, comparing, interpreting, ranking and tracking small incremental changes in at least one of an individual's and a group's assessed, and measured, and laboratory analyzed levels of total wellness, optimal health and fitness, and overall associated medical/health risks based on specific sets or groups of pre-determined pertinent, validated and cross-correlatable categories, parameters and variables of said levels, and weighing and adjusting pre-determined optimal ranges of said levels as well as standard means and standard deviation values of said method and preparing personal analyses for individuals and groups using information gathered from at least two of a series of assessed, and measured and clinically evaluated on-site and laboratory tests and measurements of at least one of individuals and groups and a scientific total wellness, optimal health and fitness, and associated medical health risks database, the method comprising the steps of:
   a. establishing a list of measurable, quantifiable, correlatable, comparable, validatable, and trackable categories, parameters and variables of said levels of total wellness, optimal health and fitness, and any overall associated medical/health risk-related information;
   b. obtaining testing data from individuals and groups corresponding to specific predetermined sets or groups of pertinent, validated and correlatable categories, parameters and variables of total wellness, optimal health and fitness, and any overall associated medical risks;
   c. creating a data gathering scheme for each said category, parameter, and variable, and combination of said categories, parameters, and variables;
   d. utilizing the scheme to gather both subjective and objective data on individuals, and groups;
   e. quantifying and compiling the data, checking the data for validity, correlating, comparing, updating and storing the quantified, compiled, validated, correlated, compared, updated and stored data as an inventory of total wellness, optimal health and fitness and any associated medical/health risk-related knowledge;

f. locally weighting and adjusting the pre-determined optimal ranges of total wellness, optimal health and fitness, and overall associated medical risks as well as the standard means and the standard deviation values of said method; and, g. preparing an evaluation of said knowledge by correlating and comparing said knowledge with: (1) ideal predetermined rankings of total wellness, optimal health and fitness and associated medical/health risks; (2) said scientific total wellness, optimal health and fitness, and any associated health risks database; and (3) any previously scientific total wellness, optimal health and fitness, and any associated health risks assessed and measured, and laboratory analyzed individuals and groups to create a report having two parts, a first part having a series of visual depictions each having analysis information categorized as:

i. excellent well-being, also known as extremely low risk,
ii. good well-being, also known as low risk,
iii. average well-being, also known as average risk,
iv. poor well-being, also known as high risk,
v. dangerous well-being, also known as extremely high risk, and a second part comprising a series individualized evaluations and recommendations for improvement, each of said second part being printed proximate a selected one of said first part for review in combination with said one of said first part.

9. The method according to claim 8 including establishing said assessed quantifiable categories as:

i. basic attitudes/outlooks, core beliefs, behavior and commitment to wellness, plus mental and emotional balance and health, self-love, and relationship(s)' wellness;
ii. eating and drinking habits, the use of natural foods, low-fat nutrition and dietary habits;
iii. regular gentle non-stressful aerobic physical activities and cardiovascular exercise habits;
iv. alcohol, smoking and drug consumption;
v. environment, health and safety behaviors, and environmental habits;
vi. use of vitamins/minerals/herbs supplements and pure water;
vii. personal physical, genetic, medical and immune histories;
viii. family physical, genetic, medical and immune histories;
ix. healthy (nurturing) relationships;
x. major stress/distress and risk evaluations;
xi. frequency and quantity of any medications used;
xii. age;
xiii. race; and
xiv. sex said categories comprising subjective non-physical assessed parameters of scientific total wellness, optimal health and fitness, and any associated medical/health risks.

10. The method according to claim 8 including establishing said measured quantifiable categories as:

i. resting heart (pulse) rates;
ii. exercise heart (pulse) rates;
iii. recovery heart (pulse) rates;
iv. oxygen utilization;
v. systolic blood pressure;
vi. diastolic blood pressure.
vii. body fat composition (the percentage of fat to muscle);
viii. circulation efficiency (stress/distress temperature);
ix. height and weight ratio;
x. type of (body) frame;
xi. urine analyses;
xii. saliva (sputum) analyses;
xiii. blood cells analyses; and
xiv. vital lung capacity pulmonary function and forced expiratory volume;

said measured categories comprising objective physiological measurements of scientific total wellness, optimal health and fitness, and any associated medical/health risks.

11. The method according to claim 8 including establishing said laboratory blood analyzed quantifiable categories as:

i. total blood cholesterol lipids;
ii. total blood triglyceride lipids;
iii. total blood LDL lipids;
iv. total blood HDL lipids;
v. total cholesterol to HDL ratio;
vi. LDL to HDL ratio;
vii. liver function;
viii. glucose;
ix. sugars;
x. proteins;
xi. vitamins;
xii. minerals;
xiii. total immune system natural killer cell (NK) activity;
xiv. total immune system vitality and NKHT3 percentage;
xv. total autoimmunology NK, B, and T-cell counts; and
xvi. immune T-cell helper/suppressor ratio;

said laboratory blood analyzed categories comprising objective laboratory parameters of scientific total wellness, optimal health and fitness, and any associated medical/health risks.

12. The method according to claim 8 including in method step "e" preparing said evaluation in the form of at least one visually accented graph, each graph having an associated report.

13. The method according to claim 12 in which said graph has a graduated 10-point scale.

14. The method according to claim 13 in which each two points of said 10-point scale depict one of said analysis information categories.

15. A system for utilizing at least two of a series of assessing, and measuring, and laboratory analyzing scientific sets or groups of pertinent, validated, correlations and predetermined categories, parameters and variables of total wellness, optimal health and fitness, and overall associated medical risks of at least one of individuals and groups, the system comprising:

a. data input means receptive of various testing data from a given person corresponding to specific predetermined sets or groups of pertinent, validated mid correlatable categories, parameters and variables of total wellness, optimal health and fitness as well as any overall associated medical risks for predicting total wellness, optimal health and fitness, and overall associated medical risks;

b. means for transforming the testing data from each pertinent, validated and correlatable category, parameter and variable to produce transformed data for each category, parameter and variable;
c. means storing a data base of transformed data from previous or other total wellness, optimal health and fitness, and any overall associated medical risks assessment systems for previously assessed, and measured, and laboratory analyzed individuals and groups;
d. means for determining the optimal ranges of total wellness, optimal health and fitness, and any overall associated medical risks as well as standard mean and standard deviation values from the database in accordance with an actual occurrence of the given outcome for previously assessed, and measured, and laboratory analyzed individuals and groups;
e. means for comparing the transformed data with any pertinent, validated and correlatable categories, parameters and variables of total wellness; optimal health and fitness, and overall associated medical risks as well as the standard means and the standard deviation values to assess, and measure, and laboratory analyze the likelihood; of given outcomes for individuals and groups;
f. means for comparing the transformed data with any pertinent, validated and correlatable optimal ranges as well as the standard mean and standard deviation values to assess, and measure, and laboratory analyze the likelihood of given outcomes for individuals and groups; and,
g. means for locally updating the data base of said system with the actual occurrence for the given individuals and groups;
h. wherein the means for determining the optimal ranges of total wellness, optimal health and fitness, and overall associated medical risks as well as the standard means and the standard deviation values includes means for locally weighting and adjusting the pre-determined optimal ranges of total wellness, optimal health and fitness, and overall associated medical risks as well as the standard means and the standard deviation values of said system for the locally updated data base, whereby the weighted and adjusted means and the standard deviation values for said system are weighted and adjusted for at least one of a particular individual's and a group's set of assessed, and measured, and laboratory analyzed parameters by said system relative to the optimal ranges of total wellness, optimal health and fitness, and overall associated medical risks as well as the standard means and the standard deviation values determined from the dam base from previous or other total wellness, optimal health and fitness, and overall associated medical/risk assessment systems.
i. and including means for preparing an evaluation of said knowledge by correlating and comparing said knowledge with (1) ideal predetermined rankings of total wellness, optimal health and fitness and associated medical/health risks; (2) said scientific total wellness, optimal health and fitness, and any associated health risks database; and (3) any previously scientific total wellness, optimal health and fitness, and any associated health risks assessed and measured, and laboratory analyzed individuals and groups to create a report having two parts, a first part having a series of visual depictions each having analysis information categorized as:
i. excellent well-being, also known as extremely low risk,
ii. good well-being, also known as low risk,
iii. average well-being, also known as avenge risk,
iv. poor well-being, also known as high risk,
v. dangerous well-being, also known as extremely high risk.

16. The system according to claim 15, further comprising means for storing predetermined requirements for total wellness, optimal health and fitness, and overall associated medical risks data comprising the testing data; all assessed, and measured, and laboratory analyzed sets or groups of pertinent, validated and correlatable categories, parameters and variables of total wellness, optimal health and fitness, and overall associated medical risks; the transformed data; the weighted and adjusted data; the determined standard means; the determined standard deviations; and the means for validating and correlating the data when received, transformed and determined with regard to the predetermined requirements and the means for indicating when the data does not meet the requirements.

17. The system according to claim 15, including means for assessing specific sets or groups of pertinent, validated and correlatable categories, parameters and variables of total wellness, optimal health and fitness, and overall associated medical risks, wherein said at least ten categories, parameters and variables are selected from the non-physical categories, parameters and variables consisting of:
i. basic attitudes/outlooks, core beliefs, behaviors and commitment to wellness, plus mental and emotional balance and health, self-love, and relationship(s)' wellness;
ii. eating and drinking habits, the use of natural foods, low-fat nutrition and dietary habits;
iii. regular gentle non-stressful aerobic physical activities and cardiovascular exercise habits;
iv. alcohol, smoking and drag consumption;
v. environment, health and safety behaviors, and environmental habits;
vi. use of vitamins/minerals/herbs supplements and pure water;
vii. personal physical, genetic, medical and immune histories;
viii. family physical, genetic, medical and immune histories;
ix. healthy (nurturing) relationships;
x. major stress/distress and risk evaluations;
xi. frequency and quantity of any medications used;
xii. age;
xiii. race; and
xiv. sex.

18. The system according to claim 15, including means for measuring specific sets or groups of pertinent, validated and correlatable categories, parameters and variables of total wellness, optimal health and fitness, and overall associated medical risks, wherein said at least ten categories, parameters and variables are selected from the physiological categories, parameters and variables consisting of:
i. resting heart (pulse) rates;
ii. exercise heart (pulse) rates;
iii. recovery heart (pulse) rates;
iv. oxygen utilization;
v. systolic blood pressure;
vi. diastolic blood pressure;
vii. body fat composition (the percentage of fat to muscle);

viii. circulation efficiency (stress/distress temperature);
ix. height and weight ratio;
x. type of (body) frame;
xi. urine analyses;
xii. saliva (sputum) analyses;
xiii. blood calls analyses; and,
xiv. vital lung capacity pulmonary function and forced expiratory volume.

19. The system according to claim 15, including means for laboratory biochemical blood analyzing specific sets or groups of pertinent, validated and correlatable categories, parameters and variables of total wellness, optimal health and fitness, and overall associated medical risks, wherein said at least twelve categories, parameters and variables are selected from the laboratory biochemical blood analyzed categories, parameters and variables consisting of:

i. total blood cholesterol lipids;
ii. total blood triglyceride lipids;
iii. total blood LDL lipids;
iv. total blood HDL lipids;
v. total cholesterol to HDL ratio;
vi. LDL to HDL ratio;
vii. liver function;
viii. glucose;
ix. sugars;
x. proteins;
xi. vitamins;
xii. minerals;
xiii. total immune system natural killer cell (NK) activity;
xiv. total immune system vitality and NKHT3 percentage;
xv. total autoimmunology NK, B, and T-cell counts; and
xvi. immune T-cell helper/suppressor ratio.

20. The system according to claim 15, wherein at least two pertinent, validated and correlatable categories, parameters and variables of total wellness, optimal health and fitness and overall associated medical risks are used and further comprising means for correlating the comparisons and correlations of the transformed data for the at least two pertinent, validated and correlatable categories, parameters and variables of total wellness, optimal health and fitness, and overall associated medical risks.

* * * * *